United States Patent [19]

Schlatter et al.

[11] 3,934,127
[45] Jan. 20, 1976

[54] GRAVITOMETERS

[75] Inventors: Gerald Lance Schlatter; Charles Eveleigh Miller, both of Boulder, Colo.

[73] Assignee: International Telephone and Telegraph Corporation, New York, N.Y.

[22] Filed: Oct. 23, 1974

[21] Appl. No.: 517,212

[52] U.S. Cl.............................. 235/151.34; 73/32
[51] Int. Cl.².................... G01N 9/00; G06F 7/00
[58] Field of Search ........ 235/151.34, 151.3; 73/30, 73/32 R, 32 A

[56] References Cited
UNITED STATES PATENTS

| | | | |
|---|---|---|---|
| 3,117,440 | 1/1964 | Wilner .................................. 73/32 |
| 3,426,593 | 2/1969 | Jacobs ........................... 73/32 A X |
| 3,477,277 | 11/1969 | Wostl................................ 73/32 X |
| 3,603,137 | 9/1971 | Banks ................................... 73/32 |
| 3,769,831 | 11/1973 | Schlatter........................... 73/32 R |
| 3,832,884 | 9/1974 | Schlatter............................ 73/32 A |
| 3,862,568 | 1/1975 | Schlatter et al..................... 73/32 A |

*Primary Examiner*—Edward J. Wise
*Attorney, Agent, or Firm*—A. Donald Stolzy

[57] ABSTRACT

Apparatus for producing a digital or analog output directly proportional to the ratio of the densities of two gases at the same temperature and pressure. The ratio is usually that of the density of a gas of interest to the density of air. One outstanding feature of this instrument resides in the use of an automatic DC current control for gas and air vibrating ferromagnetic vanes which unexpectedly provides temperature compensation. The gas vane is immersed in the gas. The air vane is immersed in air. Gas and air piezoelectrical crystals for the respective gas and air vanes produce output signals of frequencies corresponding to the vibrational frequencies of the respective gas and air vanes. In combination with other gear, phase lock loops adapted for frequency multiplication are employed and advantageously improve accuracy. Substantial economy is surprisingly achieved in solving the equation. Still another feature resides in the equipment saving involved in time sharing two long counters.

It is striking that the gravity of a fluid has been found to be directly proportional to either one of the following two expressions:

$$(T_g - T_{go})(f_a - f_{ao}')$$

and $$\left(\frac{T_g}{T_{go}} - \frac{T_a}{T_{ao}}\right)(f_a - f_{ao}')$$

where $T_{go}$ is a constant, $T_{ao}$ is a constant, $f_{ao}$ is a constant, $T_{ao}$ is a constant, $T_g$ is the sample fluid vane period, $T_a$ is the reference (e.g. air) vane period, $f_a$ is the reciprocal of $T_a$, and $f_{ao}'$ is a constant.

34 Claims, 30 Drawing Figures

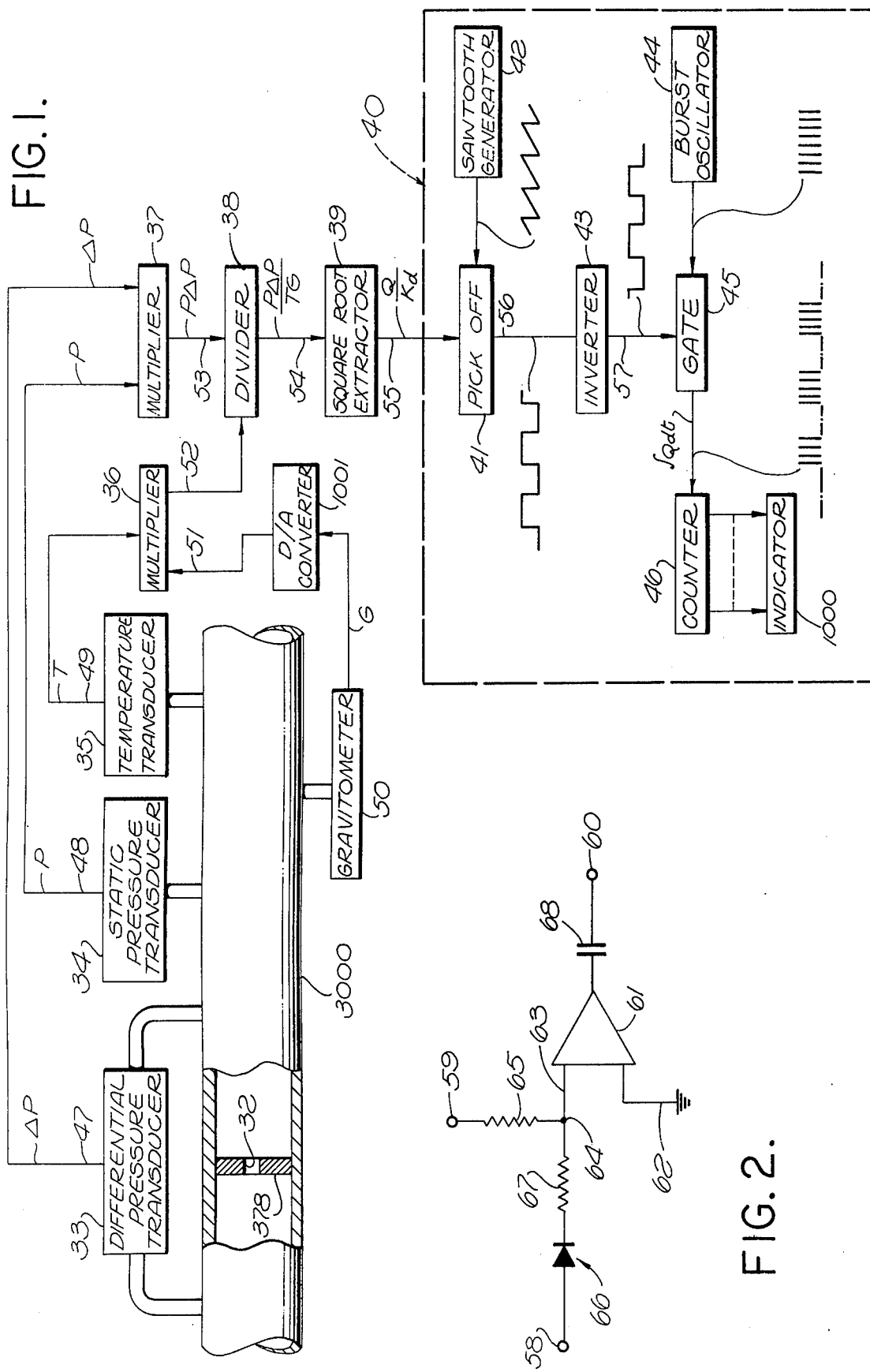

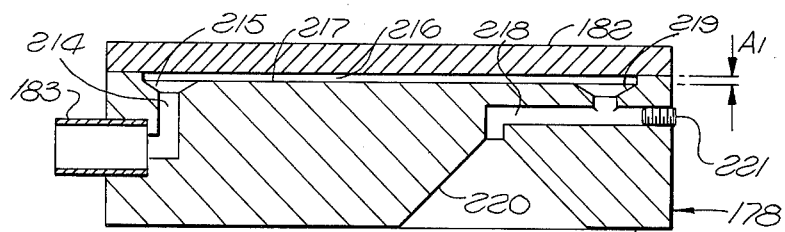
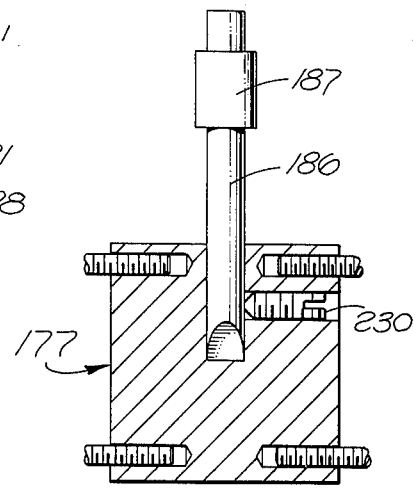
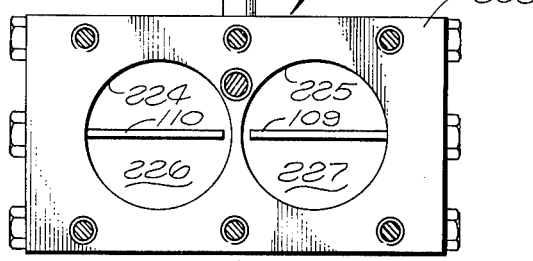
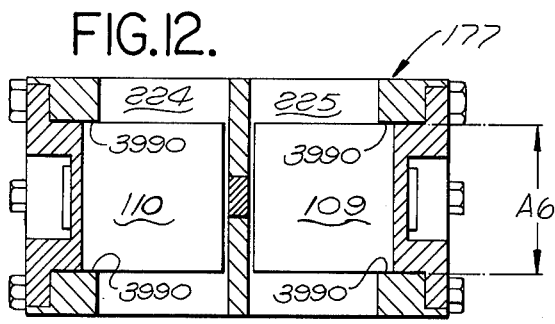
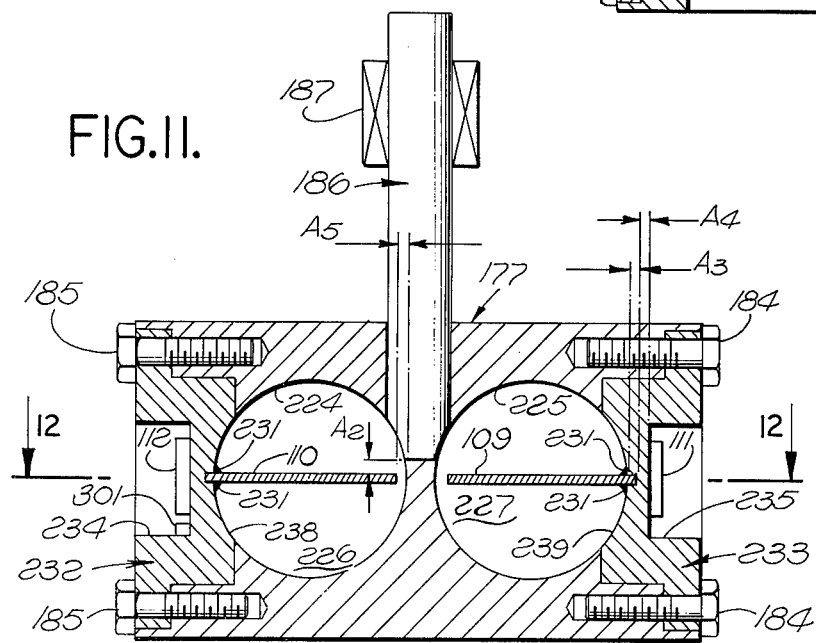

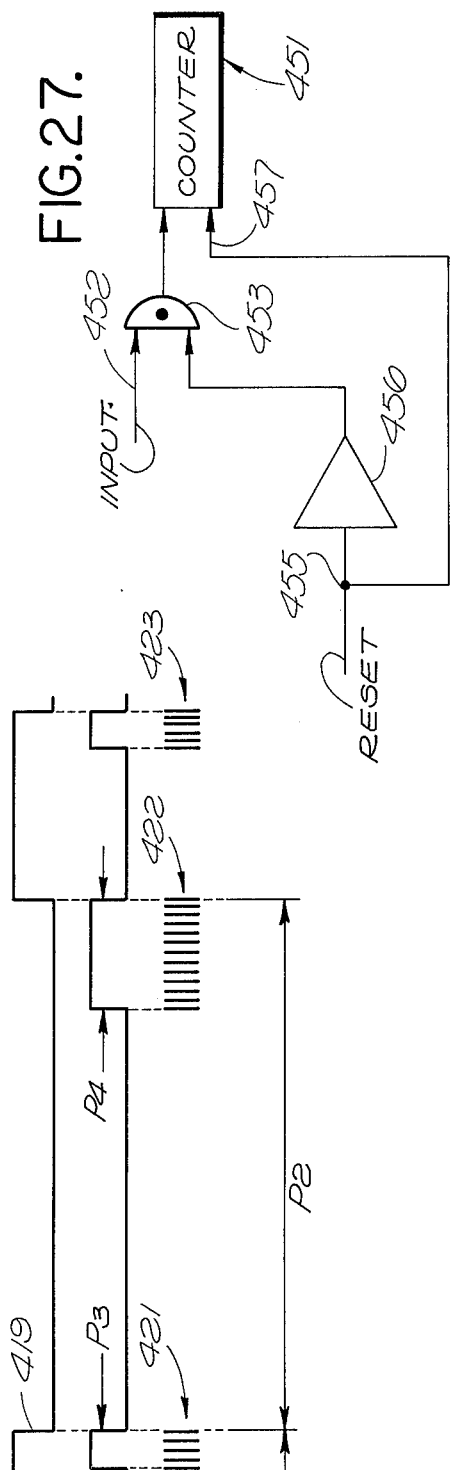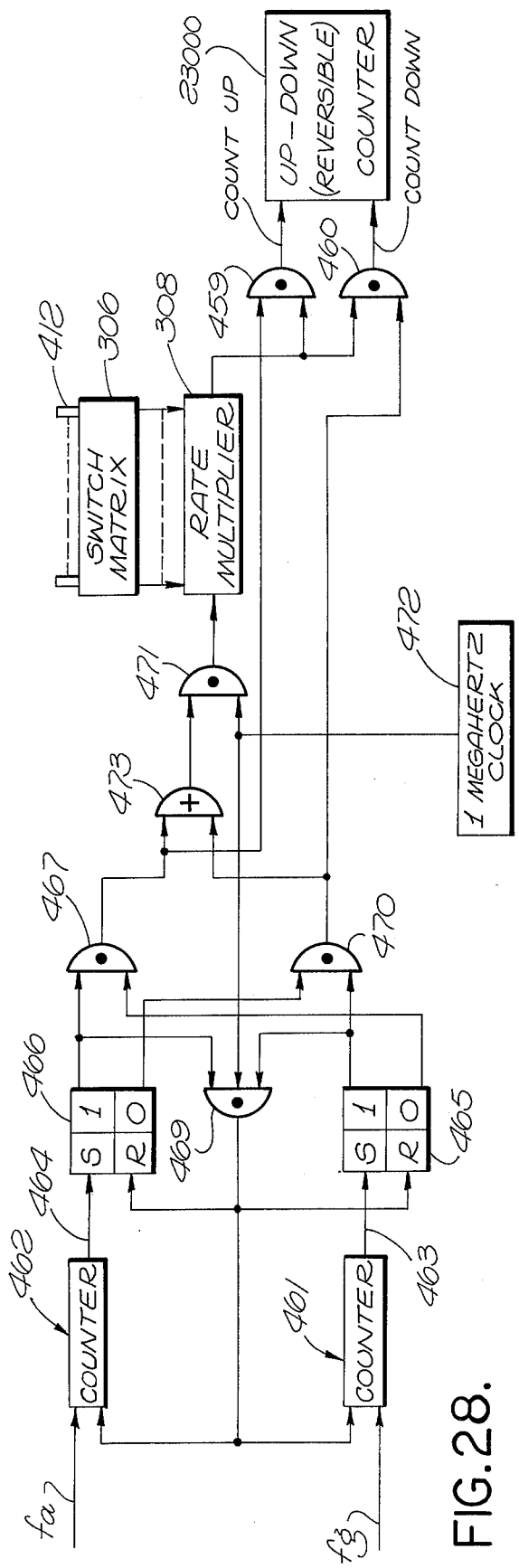
FIG. 27.
FIG. 26.
FIG. 28.

GRAVITOMETERS

BACKGROUND OF THE INVENTION

This invention relates to the art of fluid measurement, and more particularly, to apparatus for producing an output directly proportional to the ratio of the densities of two gases.

The word "gravity" is hereby defined for use herein and for use in the clamis to mean either the ratio of the densities of two fluids or the ratio of the density of a gas of any type to the density of air at the same temperature and pressure. As will be explained hereinafter, the gravity of a gas is otherwise substantially independent of temperature and pressure.

In the past, it has been practice to measure the gravity of a gas by loading a gas tight cylinder with a gas and placing it on a balance with a gas tight cylinder of air. This apparatus is expensive and cumbersome to use. Moreover, gravity is obtained by performing a batch process which cannot run continuously with flowmeter apparatus to indicate instantaneously what the rate of volume flow and the total volume flow in a pipeline is.

SUMMARY OF THE INVENTION

In accordance with the present inventin, an instantaneous indication of density or gravity or signals directly proportional thereto may be obtained through the use of a vibration densitometer having a spring metal cantilevered ferromagnetic vane.

Two such densitometers may be used in a gravitometer.

In accordance with the present invention, the gravitometer thereof may be used in one or more total volume or rate volume flow flowmeters to provide an output signal directly proportional to rate of volume flow.

The present invention may take the form of apparatus for producing a digital or analog output directly proportional to the ratio of the densities of two gases at the same temperature and pressure.

One outstanding feature of the present invention resides in the use of an automatic DC current control for gas and air vibrating ferromagnetic vanes which unexpectedly provides temperature compensation.

Gas and air piezoelectrical crystals for the respective gas and air vanes produce output signals of frequencies corresponding to the vibrational frequencies of the respective gas and air vanes. In combination with other gear, frequency multipliers employed and advantageously improve accuracy. Substantial economy is surprisingly achieved in the manner the equation is solved.

Another advantageous feature of the present invention resides in an equipment saving made possible by time sharing two long counters.

It is striking that the gravity of a fluid has been found to be directly proportional to either one of the following two expressions:

$$(T_g - T_{go})(f_a - f_{ao}') \quad (1)$$

and $$\left(\frac{T_g}{T_{go}} - \frac{T_a}{T_{ao}}\right)(f_a - f_{ao}') \quad (2)$$

where,
$T_{go}$ is a constant,
$T_{ao}$ is a constant,
$f_{ao}$ is a constant,
$T_{ao}$ is a constant,
$T_g$ is the sample fluid vane period,
$T_a$ is the reference (e.g. air) vane period,
$f_a$ is the reciprocal of $T_a$, and
$f_{ao}'$ is a constant.

The gravitometers of the present invention have a much faster speed of response and are more accurate than gravitometers of the prior art.

The gravitometers of the present invention have utility when used by themselves or in a flowmeter. For example, the output of a gravitometer constructed in accordance with the present invention may be connected to one or more process controllers, or to a DC milliammeter or recorder calibrated in gravity, or any other apparatus.

Different natural gases are frequently blended to achieve a desired BTU content based on the gas gravities.

A gravity indication is, thus, useful in estimating the BTU content of natural gas. It can be used in determining performance under gas delivery contracts specifying BTU content. Further, estimated BTU content is also frequently used for billing purposes.

As will be understood from the foregoing, automatic process controllers can be operated from the gravitometers of the present invention to maintain automatically any desired gravity or BTU content.

The above-described and other advantages of the present invention will be better understood from the following detailed description when considered in connection with the accompanying drawings.

BRIEF DESCRIPTION OF THE DRAWINGS

In the drawings which are to be regarded as merely illustrative:

FIG. 1 is a diagrammatic view of a flowmeter;

FIG. 2 is a schematic diagram of a pickup shown in FIG. 1;

FIG. 8 is a horizontal sectional view taken on the line 8—8 shown in FIG. 7;

FIG. 9 is a vertical sectional view taken on the line 9—9 shown in FIG. 5;

FIG. 10 is a vertical sectional view taken on the line 10—10 shown in FIG. 9;

FIG. 11 is a vertical sectional view taken on the line 11—11 shown in FIG. 5;

FIG. 12 is a horizontal sectional view taken on the line 12—12 shown in FIG. 11;

FIG. 13 is a perspective view of a ferromagnetic rod shown in FIGS. 5, 9, 10 and 11;

FIG. 22 is a schematic diagram of a power amplifier illustrated in FIG. 4;

FIG. 27 is a block diagram of a resetting mechanism for a counter; and

FIGS. 28, 29, 30 and 31 are block diagrams of three other alternative systems of the present invention.

DESCRIPTION OF THE PREFERRED EMBODIMENTS

THE FLOWMETER OF FIG. 1

Figure 3:
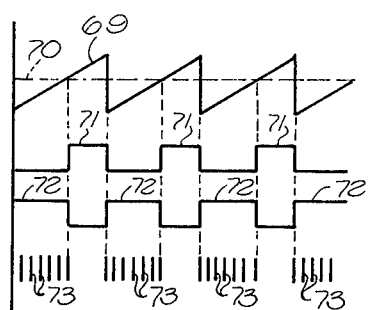
FIG. 3 is a graph of a group of waveforms characteristic of the operation of the flowmeter shown in FIG. 1.

Although the gravitometers of the present invention will have utility in a great many systems or by themselves, one use thereof is in a flowmeter, to be described.

It is well known in the prior art that the total flow $\int Q\, dt$ where $t$ is time and Q is the volume rate of gas flow per unit time, Q being measured in standard cubic feet. This standard cubic feet (at, for example, 14.7 pounds/cubic feet pressure and 68° F.) of a gas in a pipeline may be calculated from the following equation (1) defining mass flow rate Q.

$$Q = K_a \sqrt{\frac{P\Delta P}{T_1 G}} \quad (3)$$

where,

P is the static pressure in a pipeline 3000 shown in FIG. 1, $\Delta P$ is the differential pressure across an orifice 32, $T_1$ is the absolute temperature of the gas, and G is the "gravity" of the gas.

The gravity, G, of a gas is defined by $$G = \rho_g/\rho_a \quad (4)$$

where, $\rho_g$ is the density of the gas at a predetermined temperature and at a predetermined pressure, and $\rho_a$ is the density of air at the same said predetermined temperature and predetermined pressure.

It is interesting to note that G is substantially "independent" of temperature and pressure. That is, for the same gas, the value of G will be the same regardless of which "predetermined temperature" and "predetermined pressure" it is measured. The proof for this characteristic follows.

Boyle's law and Charles' law may be combined into the single expression $$PV/T_1 \quad (5)$$

which is equal to a constant. Hence, $$PV = MRT_1 \quad (6)$$

where,

P is pressure,

V is volume,

M is mass,

R is the gas constant, and $T_1$ is absolute temperature.

If $\rho$ is density, then $$\rho = \frac{M}{V} \quad (7)$$

Thus, combining (6) and (7), $$\rho = \frac{K_1 P}{T_1} \quad (8)$$

where, $$K_1 = \frac{1}{R} \quad (9)$$

Equations (10) and (11) are analogous to (8) for a gas, g, of interest and air, a.

$$\rho_g = \frac{K_{1g} P_g}{T_{g1}} \quad (10)$$

$$\rho_a = \frac{K_{1a} P_a}{T_{a1}} \quad (11)$$

Dividing (10) and (11) and assuming $P_g = P_a$ and $T_g = T_a$, $$\frac{\rho_g}{\rho_a} = \frac{K_{1g}}{K_{1a}} \quad (12)$$

Combining (4), (8) and (12), $$G = \frac{R_a}{R_g} \quad (13)$$

Equation (13), thus, indicates that G is truly "independent" of which set of temperature and pressure conditions are selected.

Equation (3) may be proven as follows. The flow, $Q_s$, through an orifice is $$Q_s = K_2 A \sqrt{2gH_g} \quad (14)$$

where, $K_2$ is a constant,

A is the orifice area, g is acceleration due to the earth's gravity, and $H_g$ is the differential pressure head in feet across the orifice.

To convert the differential head to inches of air, $$H_g = \frac{H_a \rho_a}{12 \rho_g} \quad (15)$$

Hereinafter, the 68° F. and the 14.7 pounds/square inch will be referred to as "standard temperature and pressure $T_a$ and $P_a$, respectively."

Equation (10) can, thus, be divided by equation (11) as follows:

$$\rho = \frac{K_{1a} G P}{T_1} \quad (16)$$

where,

P is equal to $P_g$, $T_1$ is equal to $T_g$, and $\rho$ is equal to $\rho_g$.

Substituting $p = p_a$ into (15), (16) into the resultant, one obtains $$H_a = \frac{H_a \rho_a T_1}{12 K_{1a} GP} \qquad (17)$$

Substituting (17) into (14), one obtains $$Q_s = K_2 A \sqrt{\frac{2g H_a \rho_a T_1}{12 K_{1a} GP}} \qquad (18)$$

Thus, $$Q_s = K_3 \sqrt{\frac{H_a \rho_a T_1}{GP}} \qquad (19)$$

where, $$K_3 = K_2 A \sqrt{\frac{2g}{12 K_{1a}}} \qquad (20)$$

From expression (5), $$\frac{PQ}{T} = \frac{P_a Q_a}{T_{a1}} \qquad (21)$$

Thus, $$Q_a = \frac{PQT_{a1}}{T_1 P_a} \qquad (22)$$

Combining (19) and (22), $$Q = K_3 \sqrt{\frac{H_a \rho_a T_1}{GP} \times \frac{PT_{a1}}{TP_a}} \text{ and} \qquad (23)$$

$$Q = K \sqrt{\frac{P \Delta P}{TG}} \qquad (24)$$

where, $$K_a = \frac{K_3 T_{a1}}{P_a} \qquad (25)$$

and $\Delta P$ is equal to $H_a \rho_a$ (pressure equals height times density).

The embodiment of FIG. 1 mechanizes equation (3) for continuously indicating total volume flow in standard cubic feet.

In FIG. 1, a portion of a pipeline is indicated at 3000 having a disc 378 fixed therein to provide an orifice 32. A differential pressure transducer 33 senses the difference between the pressures on opposite sides of orifice 32. A static pressure transducer 34 senses the pressure on one side of orifice 32. A temperature transducer 35 senses the temperature on one side of the orifice 32.

In FIG. 1, a multiplier 36, a multiplier 37, a divider 38 and a square root extractor 39 are provided. An output circuit 40 is connected from the output of square root extractor 39. Output circuit 40 includes a pickoff 41, a saw-tooth generator 42, an inverter 43, a burst oscillator 44, a gate 45 and a counter 46.

Differential pressure transducer 33 produces a DC current on an output lead 47 which is directly proportional to the difference between the pressures on opposite sides of the orifice 32.

Static pressure transducer 34 produces a DC current on an output lead 48 directly proportional to the pressure on one side of orifice 32. Temperature transducer 35 produces a DC current on an output lead 49 directly proportional to the temperature of the gas inside pipeline 3000 on one side on orifice 32. of A gravitometer 50 is connected from pipeline 3000 on one side of orifice 32 to produce a DC output current on an output lead 51 of a digital-to-analog converter 1001 directly proportional to the gravity of the gas in pipeline 3000.

Multiplier 36 is connected from leads 49 and 51. The output of multiplier 36 is impressed upon an output lead 52 which is connected to divider 38. Multiplier 36 then produces an output current in lead 52 which is directly proportional to the product of the outputs of temperature transducer 35 and gravitometer 50.

Multiplier 37 is connected from both of the pressure transducers 33 and 34 to divider 38. Multiplier 37 has an output lead 53, the current in which is directly proportional to the product of the current outputs of the pressure transducers 33 and 34. Divider 38 has an output lead 54 which carries a DC voltage directly proportional to the output of multiplier 37 divided by the output of multiplier 36. Divider 38 may, if desired, include a current-to-voltage converter at its output. A current-to-voltage converter, for example, may be simply a resistor connected from the output of divider 38 to ground.

Notwithstanding the foregoing, any component part of the invention employed to produce a current analog may be employed to produce a voltage analog.

Square root extractor 39 has an output lead 55 upon which a DC voltage is impressed which is directly proportional to the square root of the output of divider 38.

Pickoff 41 has an output lead 56 upon which a square wave is impressed. This square wave is generated by comparing the amplitude of the saw-tooth output of generator 42 with the amplitude of the DC voltage on lead 55.

Inverter 43 is connected over an output lead 57 to gate 45. Inverter 43 inverts the square wave output of pickoff 41.

It is to be noted that the dimensions of a square wave are conventionally vertical in volts and horizontal in time. The work "square," thus, has no reference to any particular relationship between the amplitude and period of such a wave. The phrase "square wave" is, therefore, hereby defined for use herein and in the claims to mean "a rectangular wave" or vice versa.

Burst oscillator 44 produces output pulses at a constant rate and at a pulse repetition frequency (PRF) which is large in comparison to the PRF of the square wave appearing on inverter output lead 57. Gate 45 is opened during the positive pulses of the square wave on lead 57, and passes pulses from the burst oscillator 44 to counter 46 during the pulses of the square wave on lead 57.

All of the parts shown in FIG. 1 may be entirely conventional, if desired, except gravitometer 50. Gravitometer 50 is constructed in accordance with the present invention, as will be explained.

Multipliers 36 and 37 may be entirely conventional voltage or current multipliers, if desired. Divider 38 may be an entirely conventional divider, if desired. Square root extractor 39 may be an entirely conventional square root extractor or function generator, if desired.

Saw-tooth generator 42, gate 45, inverter 43 and counter 46 may all be entirely conventional. Pickoff 41 may also be entirely conventional, if desired.

If desired, an indicator 1000 connected from counter 46 may be calibrated in total volume flow in standard cubic feet. Counter 46, if desired, may be an entirely conventional binary counter.

In FIG. 2, pickoff 41 is shown including input terminals 58 and 59, and an output terminal 60. An amplifier 61 is also shown in FIG. 2 connected to ground at 62 and having an input lead 63 connected to a summing junction 64. A resistor 65 is connected from terminal 59 to junction 64. A diode 66 and a resistor 67 are connected in series in that order from terminal 58 to junction 64. A capacitor 68 is connected from the output of amplifier 61 to terminal 60.

In FIG. 1, terminal 58 would be connected from saw-tooth generator 42. Terminal 59 would be connected from square root extractor 39. Output terminal 60 would be connected to inverter 43. The voltage supplied to terminal 59 by square root extractor 39 would be a negative voltage. The output signal of saw-tooth generator 42 would be a positive going voltage. It would begin at ground and increase from there to its peak value. When the potential at terminal 58 equals or slightly exceeds the negative potential at 59, amplifier 61, if it is a high gain amplifier having a gain of several hundred thousand, will produce a square wave output by being driven into saturation. The pulses at the output amplifier 61 will then have a pulse width directly proportional to the output voltage of square root extractor 39.

The saw-tooth output voltage of saw-tooth generator 42 is indicated at 69 in FIG. 3. The corresponding positive magnitude of the negative output voltage of square root extractor 39 is indicated at the horizontal line 70 in FIG. 3. The horizontal level of line 70 may vary from time to time, but will generally not vary as fast as the PRF of the saw-tooth voltage.

As shown in FIG. 3, pulses 71 are produced at the output of pickoff 41 in FIG. 1 which have a time width determined by the end of each saw-tooth 69 and a beginning which occurs where the inclined portion of each saw-tooth crosses line 70.

As shown in FIG. 3, inverter 43 has output pulses 72, the time width of which is directly proportional to the amplitude of the output signal of square root extractor 39. In FIG. 3, the portion of the output pulses of burst oscillator 44, which are counted by counter 46, are indicated at 73.

OPERATION OF THE FLOWMETER OF FIG. 1

In FIG. 1, the transducers 33, 34 and 35 produce differential pressure, static pressure and temperature analogs. The pressure analogs are multiplied together by multiplier 37. The temperature analog is multiplied by the gravity analog appearing on the output lead 51 of converter 1001 by multiplier 36. The output of multiplier 37 is divided by the output of multiplier 36 in divider 38. The square root of the output of divider 38 is taken by square root extractor 39. The analog output of square root extractor 39 is then integrated in output circuit 40. Saw-tooth generator 42, pickoff 41 and inverter 43 produce a time analog at the output of inverter 43 of the output of square root extractor 39. This is converted to a digital number which is accumulated in binary counter 46, this digital number representing total volume flow in standard cubic feet. This digital number is indicated by indicator 1000 which has one lamp for each flip-flop or stage in counter 46 or is digital and calibrated.

THE GRAVITOMETER OF THE PRESENT INVENTION ILLUSTRATED IN FIG. 4

Figure 4:
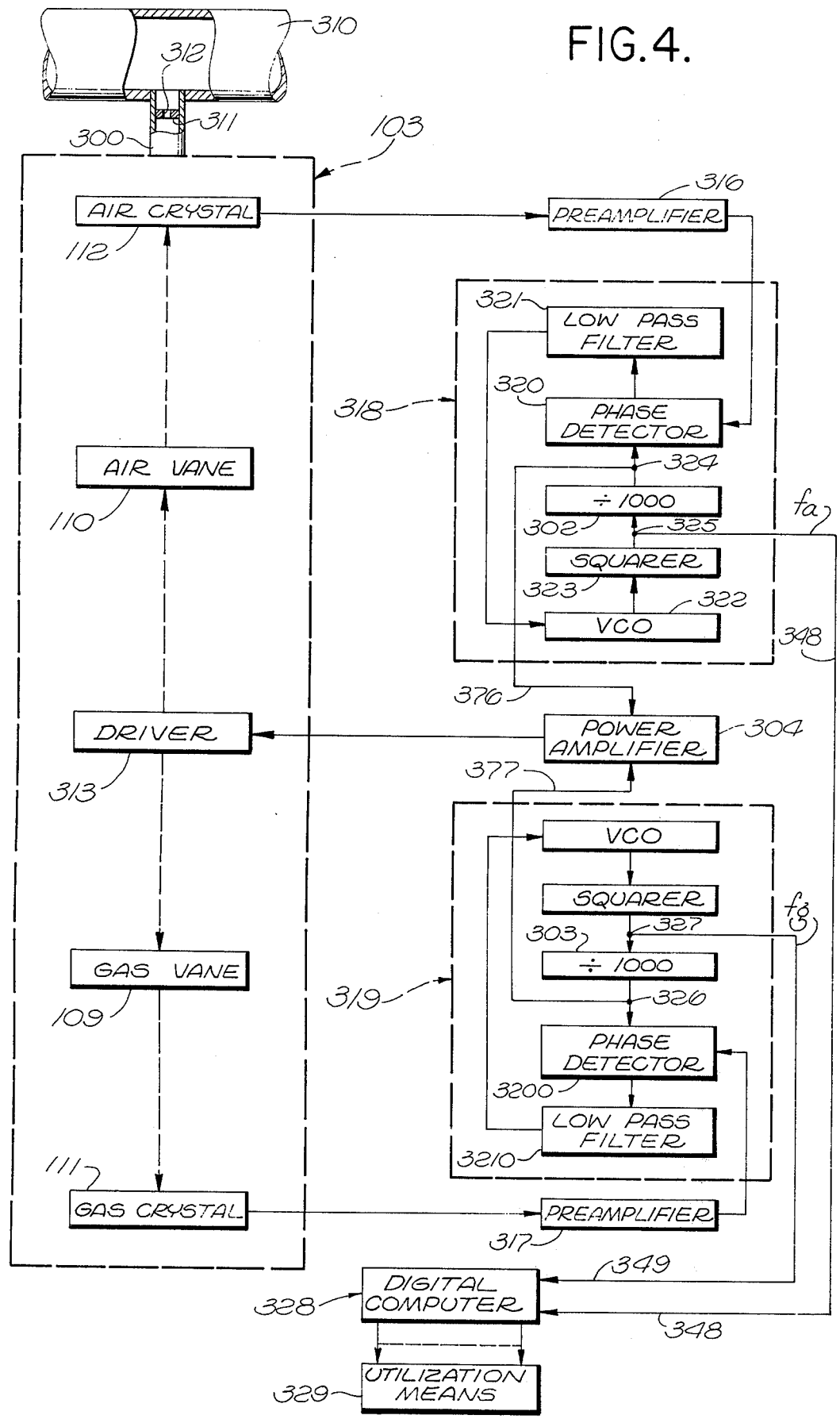
FIG. 4 is a diagrammatic view of a gravitometer constructed in accordance with the present invention.

In FIG. 4, a pipeline is illustrated at 310 having a conduit 300 connected therefrom to a twin cell assembly 103. Conduit 300 has a disc 311 sealed therein that has an orifice 312 to admit a sample of the gas flowing in pipeline 310 to assembly 103 at a relatively low flow rate and at a relatively low pressure.

Assembly 103 includes a gas vane 109 which vibrates in the gas sample, and an air vane 110 which vibrates in air at ambient temperature and pressure.

Neither of the vanes 109 and 110 vibrate naturally. There are losses. Vanes 109 and 110 must, thus, be driven. They are driven by a driver 313. Driver 313 forms a link in two combined closed loop electromechanical oscillators which oscillate both of the vanes 109 and 110 unexpectedly at different frequencies and at different rate of change of frequencies, the former being functions of respective densities.

It is a striking thing that the density of the gas and air in which vanes 109 and 110, respectively, vibrate are unexpected functions of the vane frequencies and periods.

The frequency and period of the vibration of air vane 110 is detected by a piezoelectric air crystal 112. Similarly, the frequency and period of the vibration of gas vane 109 is detected by a piezoelectric gas crystal 111. The output of air crystal 112 is connected to the input of a preamplifier 316. The output of gas crystal 111 is connected to the input of a preamplifier 317.

The output of preamplifier 316 is connected to the input of a phase lock loop 318. The output of preamplifier 317 is connected to the input of phase lock loop 319. Each of the phase lock loops 318 and 319 may or may not be identical to each other, if desired. Each of the phase lock loops 318 and 319 may be entirely conventional including adaptations which they have to produce two square wave output signals each, all four of such signals normally having different frequencies. All four output signals may have a mark-to-space ratio of unity although that is not always necessary and may never be necessary. Phase lock loop 318 has an adaptation which makes it a frequency multiplier by the addition of a divide-by-1,000 divider 302. Similarly, phase lock loop 319 has a divide-by-1,000 divider 303 which makes phase lock loop 319 a frequency multiplier as well.

In production, it is impossible to make two air vanes precisely alike. It is also impossible to make two gas vanes precisely alike. As will be explained, each vane is calibrated independently. It is impossible to predict what the vibrational frequency of air vane will be in advance. Thus, all the numerical values given herein are typical. However, these values could not be predicted with the accuracy desired for any given vane. The air vane 110 might have a vacuum frequency of 316.000 Hz. The air vane might have a frequency of 314.000 Hz. for a dry air density of 0.001205 gram per milliliter at 20° C. and at 760 millimeters of Mercury. Call this density $d_c$. For a density of $2d_c$, the air vane may have a frequency of 312.025 Hz.

Again, typically, the gas vane 109 may have a vacuum frequency of 314.000 Hz. At $d_c$, the gas vane frequency may be 312.000 Hz.

Phase lock loop 318 has a phase detector 320, the output of which is impressed upon a low pass filter 321. Low pass filter 321 may or may not have an amplifier. Similarly, amplifiers and inverters may be omitted or added throughout this disclosure, as desired.

The loop is closed by connection from low pass filter 321 through a voltage controlled oscillator (VCO) 322, a squarer 323, divider 302 to phase detector 320.

Squarer 323 may be omitted in some or all cases. It is conventional to employ a VCO which has a square wave output.

Phase lock loop 318 has an output junction 324 connected from the output of divider 302, and an output junction 325 connected from the output of squarer 323. Similarly, phase lock loop 319 has an output junction 326, and an output junction 327.

Because both of the phase lock loops 318 and 319 may be identical, the remaining details of phase lock loop 319 will not be described.

The output from junction 324 in phase lock loop 318 is connected to one input of a power amplifier 304. Similarly, the output junction 326 of phase lock loop 319 is connected to the other input of power amplifier 304.

The power amplifier 304 has an output which is connected to driver 313 in assembly 103.

Junctions 325 and 327 in phase lock loops 318 and 319 are connected to a digital computer 328 which, in turn, is connected to utilization means 329.

In accordance with the foregoing, the frequencies appearing at junctions 324 and 326 in phase lock loops 318 and 319, respectively, for a gas density of $d_c$ and an air density of $d_c$ may, for example, be 312.000 Hz. and 314.000 Hz., respectively. On the other hand, the corresponding frequency of the square wave having the legend $f_a$ will have a frequency for a density $d_c$ of 314,000 Hz. The lead having the legend $f_g$ will have a corresponding frequency for gas density of $d_c$ equal to 312,000 Hz.

In accordance with the foregoing, $f_a$ is directly proportional to or equal to the air vane frequency depending upon whether the multiplication factor of frequency multiplier 318 is something other than 1.0 to 1.0, respectively. Similarly, $f_g$ is directly proportional to or equal to the gas vane frequency depending upon whether the multiplication factor of frequency multiplier 319 is something other than 1.0 or 1.0, respectively.

Digital computer 328 converts the inputs thereto labeled $f_a$ and $f_g$ to a digital number which is directly proportional to the gravity of the gas flowing in pipeline 310.

The instrument as illustrated in FIG. 4 may be sold without the utilization means 329. The utilization means 329 may take many forms. The gravitometer of the present invention may be used in larger computation systems. It may be used as gravitometer 50 in the flowmeter of FIG. 1 or in any other systems. It may be employed in process control systems. Utilization means 329 may, thus, be a flowmeter, a process control system, simply means to indicate the gravity of the gas flowing in pipeline 310 or otherwise. For this reason, the phase "utilization means" is defined for use herein and for use in the claims to mean a flowmeter, another system, a process control system, an indicator, or otherwise.

THE TWIN CELL ASSEMBLY 103 ILLUSTRATED IN FIGS. 5-15

Figure 5:
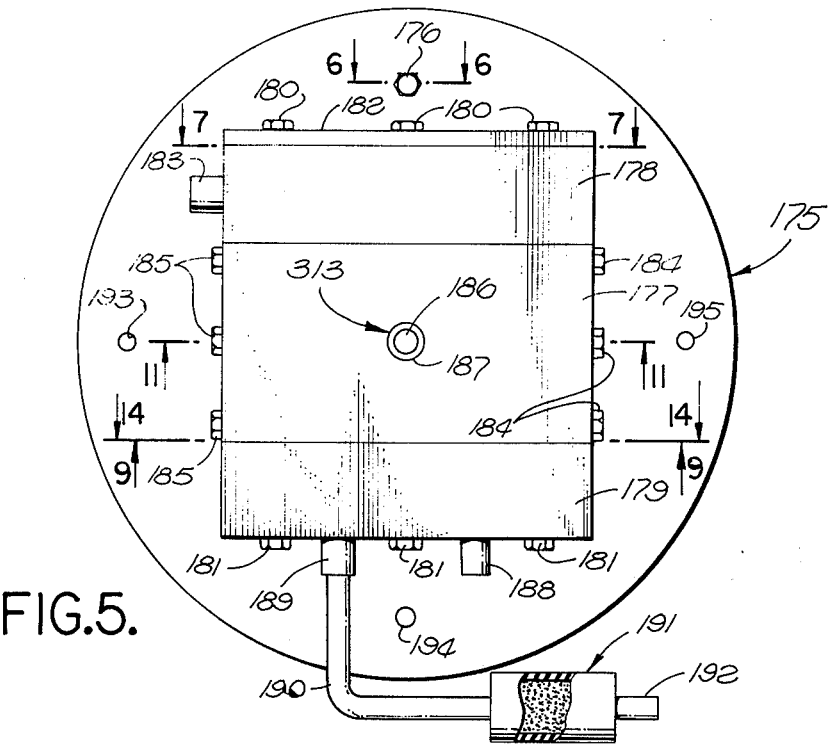
FIG. 5 is a top plan view of a twin cell assembly indicated diagrammatically in FIG. 4.

A top plan view of assembly 103 is shown in FIG. 5 including a supporting plate 175, a supporting bolt 176, a central block 177, an inlet block 178 and an outlet block 179. Inlet block 178 is fixed to central block 177 by six cap screws 180, only three of which are shown in FIG. 5. Similarly, outlet block 179 is fixed to central block 177 by six cap screws 181. A cover plate 182 is positioned between the heads of screws 180 and inlet block 178. Inlet block 178 has an inlet ferrule 183 into which conduit 300 may be inserted and sealed.

Four cap screws 184 fix a subassembly to block 177. Similarly, four cap screws 185 fix another subassembly to block 177. Both of the said subassemblies will be described hereinafter.

Driver 313 includes a ferromagnetic rod 186 which projects into and is fixed relative to block 177, as will be described. A driver coil 187 is fixed relative to rod 186 therearound.

Outlet block 179 carries gas and air vent ferrules 188 and 189, respectively, that are fixed relative thereto. A conduit 190 is inserted into ferrule 189 and may be sealed therein, if desired. A dessicator 191 is connected from conduit 190 and has a vent tube 192 allowing air to pass back and forth through dessicator 191 from the atmosphere into and out of block 177, respectively.

Only one bolt 176 is shown in FIG. 5. However, four bolts are preferably employed. Other bolts would pass through holes 193, 194 and 195 in plate 175, as shown in FIG. 5.

Figure 6:
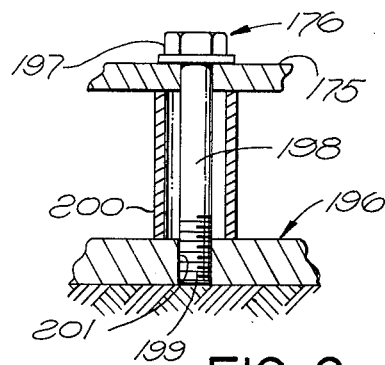
FIG. 6 is a vertical sectional view taken on the line 6—6 through a mounting bolt shown in FIG. 5.

All the structures shown in FIG. 6 are fixed relative to each other. A plate 196 is provided below plate 175. Bolt 176 has a head 197 that rests on top of plate 175, a shank 198 which is slidable therethrough and a threaded lower end 199 which is threaded into plate 196. A cylindrical spacer 200 is held in axial compression between plates 175 and 196, bolt shank 198 extending through the center of spacer 200.

Plate 196 has four threaded holes 201, only one of which is shown in FIG. 6. The other three holes lie substantially in registration with holes 193, 194 and 195, respectively, of plate 175.

Figure 7:
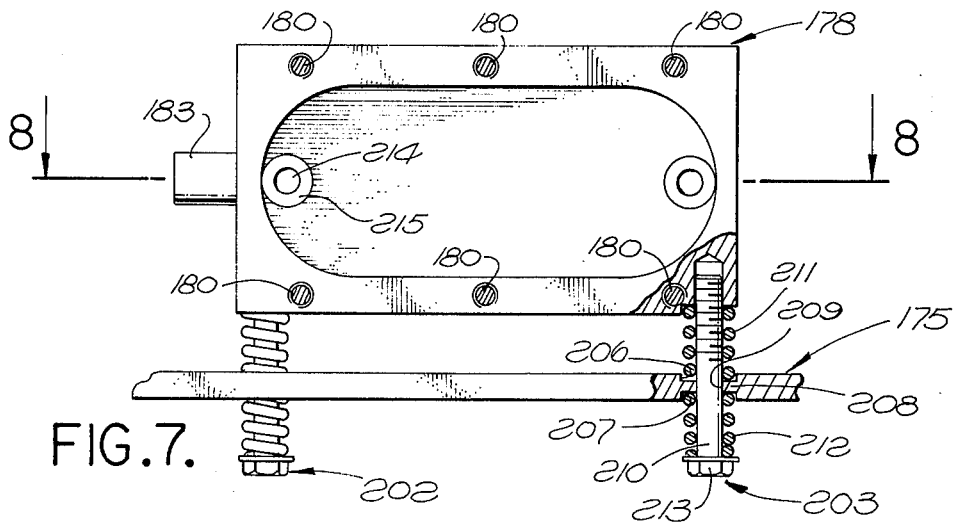
FIG. 7 is a vertical sectional view taken on the line 7—7 shown in FIG. 5.

As shown in FIG. 7, block 178 has two cap screws 202 and 203 fixed relative thereto. The structure immediately surrounding screw 202 is substantially identical to that surrouding screw 203. Thus, the structure immediately surrounding screw 203 will be the only structure described. The same is true of the structure surrounding screws 204 and 205 in FIG. 14. In FIG. 7, plate 175 is recessed at 206 and 207. Plate 175 has a web 208 which separates the recesses 206 and 207. Web 208, itself, has an opening 209 therethrough through which the shank 210 of screw 203 projects. Screw shank 210 is, thus, slidable through opening 209. A spring 211 is trapped and held in compression between web 208 and the lower end of block 178, as viewed in FIG. 7. A spring 212 is trapped and held in compression between web 208 and the head 213 of screw 203. A resilient mounting is, thus, provided for all the structure above plate 175 which is fixed relative to screws 202, 203, 204 and 205.

Screws 180, shown in FIGS. 5 and 7, are slidable through corresponding holes in plate 182 and block 178 and threaded part way into block 177.

As shown in FIG. 8, gas can be introduced into block 178 through a conduit 214 therein through a frusto-conical port 215 into a thin space 216. A number of the relative dimensions shown herein may be employed, if desired. Space 216 is defined by a recess 217 in block 178 shown in FIG. 8. Gas can then enter a conduit 218, shown in FIG. 8, through another frusto-conical port 219. A larger frusto-conical outlet surface 220 then lies in communication with conduit 218. One end of conduit 218 is closed by a screw 221 threaded thereinto and sealed therein.

As shown in FIG. 8, the depth of recess 217 is quite small and is represented by the dimension A1. It is, thus, possible to equalize the temperatures of the gas and air in block 177, to be described. Preferably, blocks 177, 178 and 179 are made of 302 stainless steel or are made of 303 stainless steel. Blocks 177, 178 and 179 may be made of these or any other conventional materials which have a fairly good thermal conductivity and are nonmagnetic. However, it makes little difference whether or not any of the cap screws shown in FIGS. 5, 6, 7 and 14 are or are not magnetic. They may or may not be magnetic, as desired.

The lower face 222 of block 178, shown in FIG. 8, fits on the face opposite 223 of block 117, shown in FIG. 9, with the cylindrical surface 225, shown in FIG. 9, having an axis that is the same as that of conical surface 220, shown in FIG. 8. The width and heights of blocks 177, 178 and 179 are all the same. They also are all aligned as in FIG. 5.

As shown in FIG. 9, another cylindrical surface is provided at 224. Cylindrical holes 224 and 225 extend completely through the width of block 177, spaces inside thereof being mostly defined by the surfaces 224 and 225. These spaces may be hereinafter referred to as the gas chamber 226 and the air chamber 226. Note that surface 222 in FIG. 8 closes one end of air chamber 226.

Air vane 110 extends into air chamber 226. Gas vane 109 projects into gas chamber 227.

As shown in FIG. 10, rod 186 is fixed in block 177 by a set screw 230. Rod 186 and set screw 230 may also be sealed therein, if desired. As shown in FIG. 11, vanes 109 and 110 and silver soldered at 231 to respective circular inserts 233 and 232 fixed relative to block 177 by screws 184 and 185, respectively.

Inserts 232 and 233 have respective recesses 234 and 235 at the bottom of which piezoelectric crystals 112 and 111 are bonded with any conventional agent such as a conventional epoxy.

A device 301, to be described further, is fixed relative to insert 232.

In FIG. 11, note will be taken that the lower end of rod 186 is disposed slightly above the upper surface of vane 110, as viewed in FIG. 11.

If desired, vanes 109 and 110 may be identical. Moreover, the upper and lower surfaces thereof may lie in two corresponding single planes. Certain symmetry will be evident from FIGS. 11 and 12.

The location of the lower end of rod 186 above the vanes is indicated at A2 in FIG. 11.

As shown in FIG. 11, inserts 232 and 233 have cylindrical portions 238 and 239, respectively, which mate with the cylindrical surfaces 224 and 225. respectively.

Note will be taken that each vane is set the same distance in a corresponding insert in a notch therein which has a depth A3, shown in FIG. 11. The nearest vane edges are, thus, spaced distances from the crystals equal to A4, shown in FIG. 11.

As shown in FIG. 13, rod 186 may have a flat 240 for set screw 230.

Figures 14, 15:
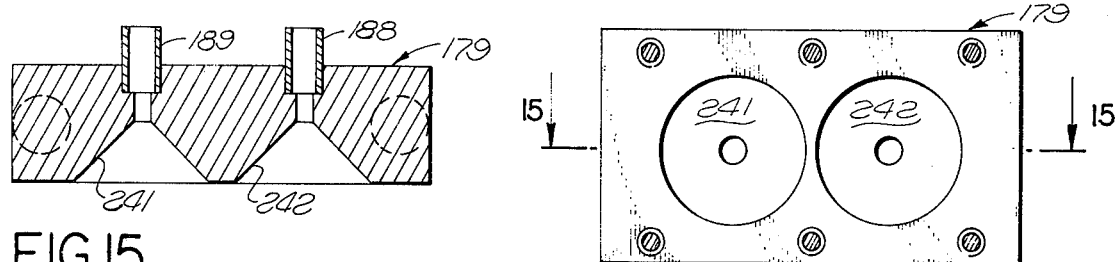
FIG. 14 is a vertical sectional view taken on the line 14—14 shown in FIG. 5.
FIG. 15 is a horizontal sectional view taken on the line 15—15 shown in FIG. 14.

As shown in FIGS. 14 and 15, block 179 has frusto-conical surfaces 241 and 242 partially defining spaces from which air and gas are vented to the atmosphere, respectively, through ferrules 189 and 188, respectively.

The air and gas flow into and out of block 177, shown in FIG. 5, may or may not be perfectly fluid tight, as desired. It will be noted that, when operating at very how pressures, the need for sealing, in some cases, may not practically exist.

In FIG. 11, if desired, dimension A5 may be .015 inch, but this dimension is not critical. Similarly, in FIG. 11, dimension A2 may be 0.03 inch, but this dimension is not critical. Surfaces 224 and 225 may have a diameter of 1 inch. Vanes 109 and 110 may each have a maximum horizontal dimension, as viewed in FIG. 11, of 1 inch. Again, the 1 inch dimension is not critical.

Assuming the foregoing dimensions, in FIG. 11, dimensions A3 would then be 0.015 inch. Dimension A4 might typically be 0.005 inch, but, again, this dimension is not critical.

Inserts 232 and 233, shown in FIG. 11, may be perfect solids of revolution except for surfaces 238 and 239. However, the inserts 232 and 233 need not be of this particular configuration. For example, insert 232 could be a solid of revolution about a horizontal axis in the plane of the drawing of FIG. 11 about which the cylindrical surface of recess 234 is concentric. Surface 238 is a portion of a surface of revolution bounded by two planes intercepting the same through the axis of chamber 227. The radius of surface 238 is, thus, ½ inch, assuming the dimensions used are those given hereinbefore. A mathematical cylinder defined by a cylindrical surface of a diameter of 1 inch would, thus, lie congruent with surfaces 238 and 239 in FIG. 11.

That portion of the apparatus shown in FIG. 11 may be considered to be, if desired, precisely symmetrical about a plane perpendicular to the drawing through the axis of rod 186. However, perfect symmetry is, of course, not a requirement. In other words, inserts 232 and 233 may be identical, although that is not required.

Vanes 109 and 110 preferably are made of Ni-Span-C, a conventional magnetic material. However, the use of this magnetic material is not critical. The material Ni-Span-C is preferred because it has a very low thermal coefficient of expansion. The material Ni-Span-C is old and well known in the art, by itself.

In FIG. 12, dimension A6 may be 1.0 inch, if desired. However, this dimension is not critical.

Each of the vanes 109 and 110 may have a thickness of 0.010 inch, although this thickness is not critical. If desired, vanes 109 and 110 may be silver soldered to inserts 233 and 232, respectively, in slots slightly larger than 0.010 inch. Such insert slots are preferably no larger than is necessary to permit an easy sliding fit of the vanes thereinto.

Preferably, the free vibratable ends of vanes do not touch the contiguous surfaces of block 177.

All gas and air connections herein, if desired, may be made with any conventional sealent such as that sold under the trademark, "Locktite," but as explained previously, this is not necessarily required.

THE ALTERNATIVE TWIN CELL ASSEMBLY 503 ILLUSTRATED IN FIGS. 16–20

Figure 16:
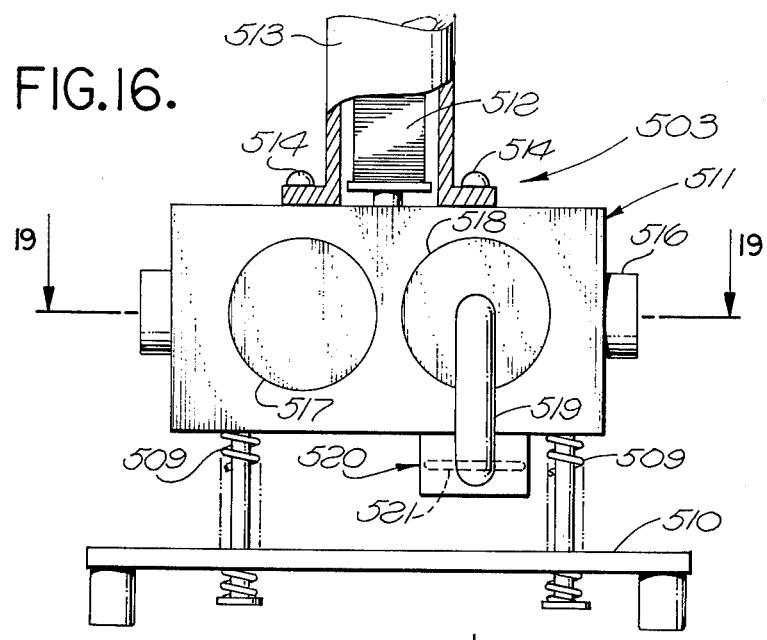
FIG. 16 is a rear elevational view of an alternative gravity cell constructed in accordance with the present invention.

An alternative gravity cell 503 is shown in FIG. 16 and is mounted resiliently on springs 509 relative to a fixed plate 510. Cell 503 includes a block 511 which may be identical to much of the construction of blocks 177, 178 and 179 shown in FIG. 5, with these three blocks welded together in a gas tight manner.

In FIG. 16, a drive coil 512 is fixed relative to block 511, as before. Drive coil 512 has a cover 513 which is fixed to block 511 by cap screws 514.

Block 511 has projections 517, 518, 527 and 528. A connecting tube 519 exits from projection 518 and enters a thermally conductive block 520 having a slot 521 therein.

Figure 20:
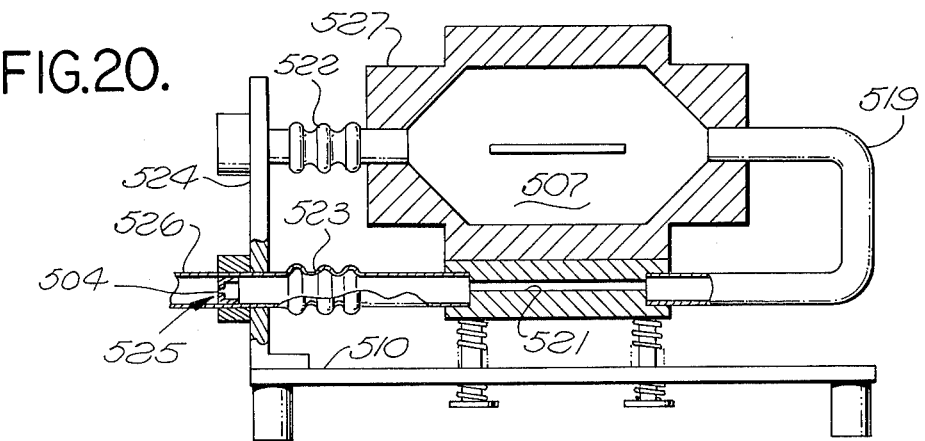
FIG. 20 is a vertical sectional view of the cell taken on the line 20—20 shown in FIG. 17.

As before, block 511, including projections 517, 518, 527 and 528, may be made of a thermally conductive metal. The same is true of block 520. As shown in FIG. 20, tube 519 being hollow, the chamber 507 is filled with gas through a flexible bellows 522. This gas is circulated through tube 519, slot 521 and out through flexible bellows 523. The left ends of bellows 522 and 523 are mounted on a plate 524. Plate 524, in turn, is fixed relative to plate 510.

Figure 17:
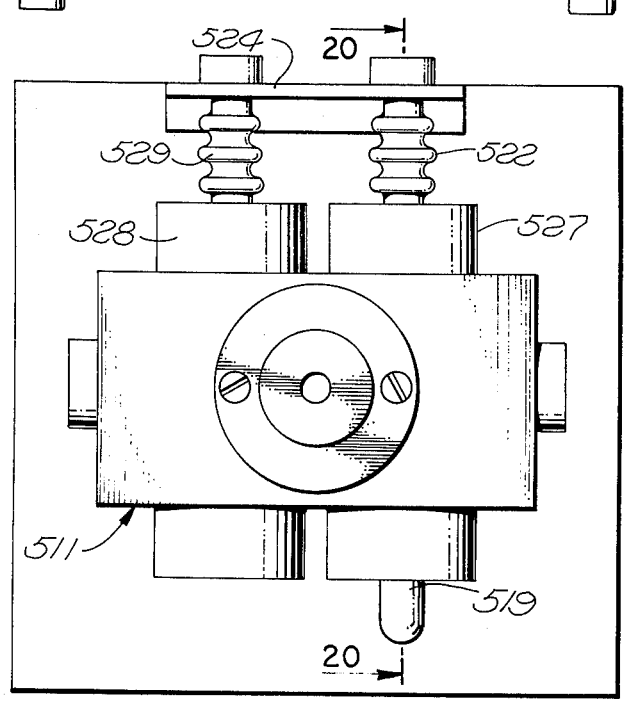
FIG. 17 is a top plan view of the cell shown in FIG. 16.
Figure 18:
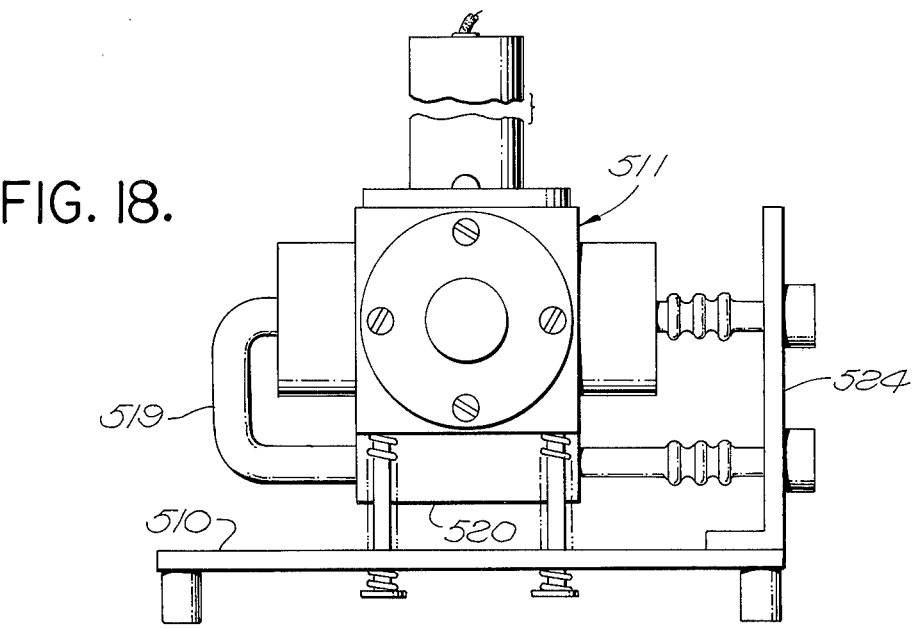
FIG. 18 is a side elevational view of the cell shown in FIG. 17.

As shown in FIG. 17, projections are provided at 527 and 528.

In FIG. 17, a flexible bellows 529 is connected from plate 524 to projection 528. See also FIG. 19.

Figure 19:
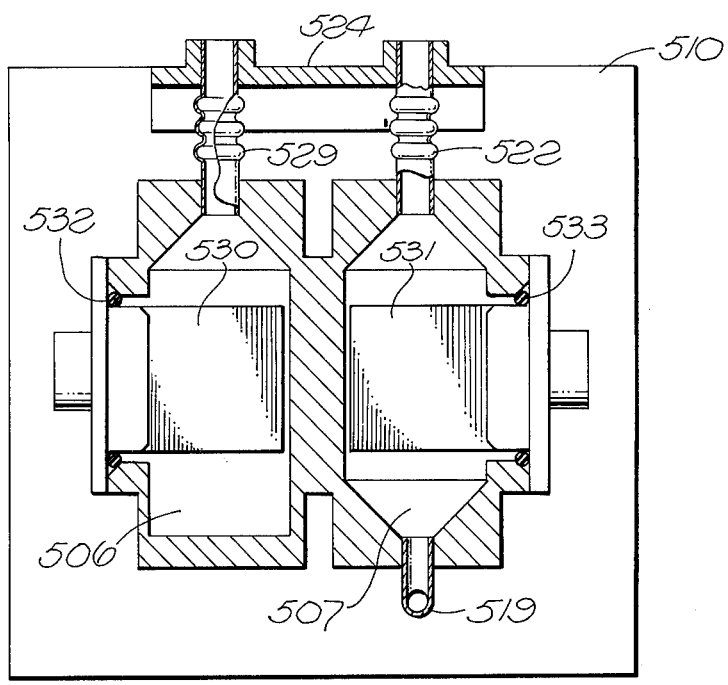
FIG. 19 is a transverse sectional view of the cell taken on the line 19—19 shown in FIG. 16.

In FIG. 19, the gas chamber 507 and the air chamber 506 are shown. Cantilever leaf spring vanes 530 and 531 are vibrated in a manner identical to the manner in which vanes 109 and 110 are vibrated. Moreover, the size and shape of vanes 530 and 531 may be identical to those of vanes 109 and 110. The same is true of their mountings, except that gas tight seals are provided by O-rings 532 and 533, respectively.

THE PREAMPLIFIER OF FIG. 21

Figure 21:
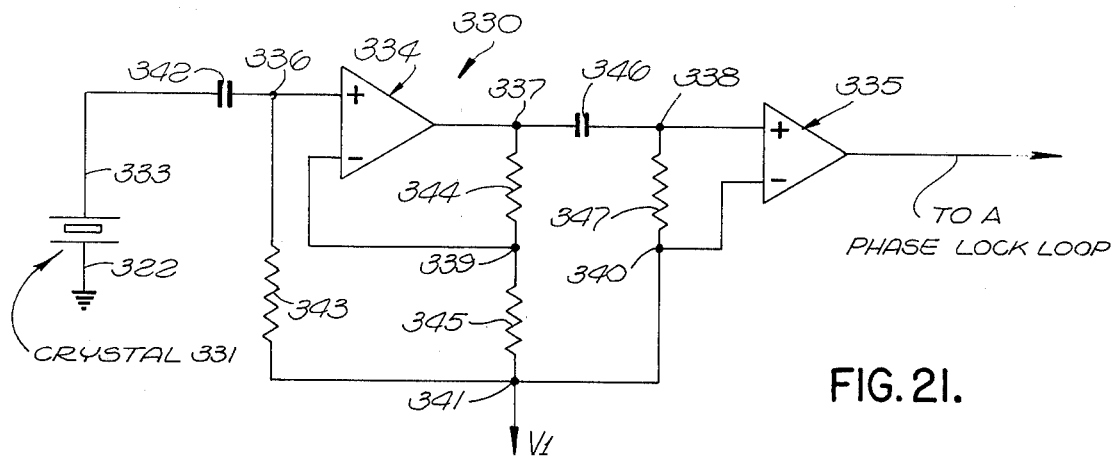
FIG. 21 is a schematic diagram of a preamplifier shown in FIG. 4.

A preamplifier 330 is illustrated in FIG. 21 including a piezoelectric crystal 331 having one side grounded at 322 and an output lead 333. Differential amplifiers are illustrated at 334 and 335. Junctions are provided at 336, 337, 338, 339, 340 and 341. Junction 341 is connected to potential VI. A typical value for VI is 2.5 volts. A typical value for V2, referred to hereinafter, is 24.0 volts.

A capacitor 342 is connected from lead 333 to junction 336. Junction 336 is connected to the noninverting input of amplifier 334. A resistor 343 is connected between junctions 336 and 341. The inverting input of amplifier 334 is connected from junction 339. The output of amplifier 334 is connected to junction 337. A resistor 344 is connected between junctions 337 and 339. A resistor 345 is connected between junctions 339 and 341. Junctions 340 and 341 are connected together. The inverting input of amplifier 335 is connected from junction 340. A capacitor 346 is connected between junctions 337 and 338. A resistor 347 is connected between junctions 338 and 340. The noninverting input of amplifier 335 is connected from junction 338. The output of amplifier 335 is then connected to a phase lock loop. Crystal 331 may be crystal 112 or crystal 111. Each of the preamplifiers 316 and 317 may, if desired, be identical to preamplifier 330 shown in FIG. 21.

THE POWER AMPLIFIER 304 OF FIG. 22

A schematic diagram of the power amplifier 304 is shown in FIG. 22. Power amplifier 304 does more than merely amplify the input signals thereto, as will be explained now and hereinafter.

As shown in FIG. 4, power amplifier 304 has input leads 376 and 377, which are also shown in FIG. 22. Junctions are provided at 700, 701, 702, 703, 704, 705, 706, 707, 708, 709, 710, 711, 712 and 713. Junction 700 acts as a summing junction. It sums the square waves appearing on leads 376 and 377, and a DC voltage which may or may not vary due to the flow of current through a resistor 355 connected between junctions 700 and 711. A capacitor 356 and a resistor 357 are connected in succession in series in that order from lead 376 to junction 700. Similarly, a capacitor 358 and a resistor 359 are connected in succession in series in that order from lead 377 to junction 700. A differential amplifier is provided at 360 having its noninverting input connected from junction 700.

In FIG. 22, a double-pole, double-throw switch 714 is provided. This switch will not ordinarily be employed. Instead, the connections of a thermistor illustrated at 301 (device 301 in FIG. 11 is the thermistor 301) will be made manually. Thermistor 301 can be located anywhere on the twin cell assembly. Thermistor 301 is to be connected in a bridge in a manner such that the DC current in coil 187 is changed. This change reduces the temperature error by a factor of 10. That is, the rate of change of gravity produced by the instrument with respect to temperature is reduced by a factor of 10. For example, such a rate may be reduced from $10^{-5}$ per degree Fahrenheit to $10^{-6}$ per degree Fahrenheit. This temperature compensation is not only unexpected ana unobvious, but inexplicable.

The reason switch 714 is shown is that, when the gravitometer is being calibrated, it is not known whether or not the rate of change of gravity with respect to temperature is a positive or a negative number. Thus, the connection of thermistor 301 is made manually, and normally is never changed from the time it is so connected at the factory.

As a matter of convenience, a potentiometer 716 is provided having a winding 717 connected between junctions 702 and 706. Potentiometer 716 has a wiper 718. The position of wiper 718 is conventionally adjusted so that the temperature error is zero at room temperature, i.e. 75° F. Notwithstanding the foregoing, the potentiometer 716 may be omitted entirely, if desired. The same is employed in production primarily to cause the gravitometer of the present invention to have exactly the same characteristics as all those which are produced. A differential amplifier 719 is provided having a noninverting input lead connected from junction 707, and an inverting input lead connected from junction 709. The output of amplifier 719 is connected to junction 711. Junctions 710 and 711 are connected together. A potentiometer 720 having a winding 721 and a resistor 722 are provided. Winding 721 and resistor 722 are connected in series in succession in that order from junction 710 to junction 708 forming a feedback path for amplifier 719. Junctions 708 and 709 are connected together. Potentiometer 720 has a wiper 723 connected from junction 710, the adjustment of which wiper 723 determines the rate of change of DC current through coil 187. It is the adjustment of wiper 723 which determines the temperature correction.

In calibration, the circuit and the entire gravitometer are maintained at the said room temperature, and wiper 718 is adjusted so that, with a gas of a known gravity the indicator of the instrument indicates the correct gravity. The entire circuit and the entire gravitometer are then raised to an elevated temperature such as 175° F., at which point wiper 723 is adjusted until the gravitometer indicator indicates the gravity of a gas passing therethrough, the gravity of the gas passing therethrough being known.

Junction 703 is connected to potential V2. Junctions 701, 702 and 703 are connected together. Junctions 705 and 706 are connected together.

Switch 714 has one pole 724 engageable either with a contact 725 or a contact 726. Switch 714 also has a pole 727 ganged with pole 724 engageable either with a contact 728 or a contact 729.

The temperature compensation circuit is generally indicated at 730. The bridge circuit is generally indicated at 731. Bridge circuit 731 has terminals 732, 733 and 734. Terminal 733 is generally at the center between two legs of the bridge. Junction 704 is connected from terminal 733. A resistor 735 is connected from junction 704 to junction 709.

Contacts 725 and 729 are connected to terminal 732. One side of thermistor 301 is connected to terminal 733. Pole 727 is connected to terminal 733 through junction 704.

The other side of thermistor 301 is connected to pole 724. Terminal 734 is connected from both of the contacts 726 and 728.

In the position shown, thermistor 301 is connected in one upper leg of the bridge 731, and terminals 733 and 734 are jumpered. Conversely, when switch 714 is moved to the position not shown, thermistor 301 is placed in a lower leg of the bridge, and terminals 732 and 733 are jumpered.

Whether or not switch 714 is used, thermistor 301 is connected in one leg of the bridge as aforesaid. It then can be switched to the other leg. Whether or not the thermistor should be in one leg or the other can be determined by reading the gravitometer indicator. Thermistor 301 is then either left in the leg where the temperature correction is the greatest, or it is moved to the other leg where the temperature correction is the greatest.

A zener diode 736 is connected between junctions 701 and 705 for voltage regulation. A resistor 737 is connected between junctions 703 and 707. A resistor 738 is connected between junctions 707 and 706. A resistor 739 is connected from terminal 734 to junction 705. A resistor 740 is connected from junction 706 to ground.

A resistor 800 is connected between terminal 732 and junction 701. A resistor 801 is connected from potentiometer wiper 718 to junction 708.

Amplifier 360 has a feedback connection 741 from junction 712 to the inverting input lead thereof. The output of amplifier 360 is connected to a base 742 of a transistor 743 via a resistor 744. Transistor 743 has a collector 755 connected to junction 713 and an emitter 756 connected to junction 712. A resistor 757 is connected from junction 712 to potential V2. A capacitor 758 and a resistor 759 are connected in succession in that order in series from junction 713 to ground. Coil 187 is also connected from junction 713 to ground.

The current through resistor 355 determines the voltage thereacross and determines the DC current through driver coil 187. Such a DC current is desirable to keep air and gas vanes 110 and 109 from vibrating at frequencies twice the frequencies of the signals $f_a/1,000$ and $f_g/1,000$. Note will be taken in FIG. 11 that regardless of the direction of current in driver coil 187, when such current reaches a maximum, vanes 109 and 110 will be attracted to rod 186. Control of the current of driver coil 187 also provides automatic temperature compensation, as has been explained.

Figure 23:
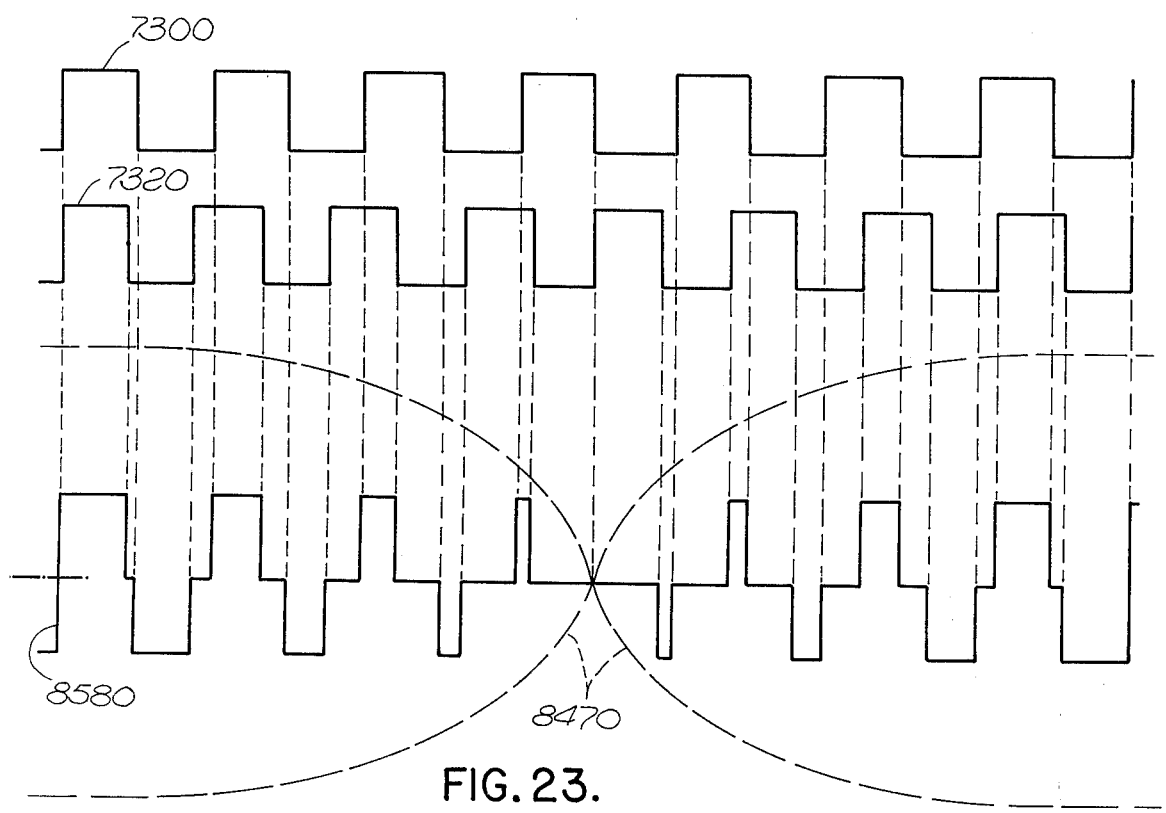
FIGS. 23 and 24 are graphs of waveforms characteristic of the operation of the power amplifier.

In FIG. 23, square waves 7300 and 7320 at the outputs of dividers 302 and 303, respectively, are indicated. When square waves 7300 and 7320 are added together, the waveform 8580 is obtained. From the following Fourier analysis of the waveform 8580, by inspection, the envelope 8470 of the fundamental may appear as shown in dotted lines in FIG. 23.

Figure 24:
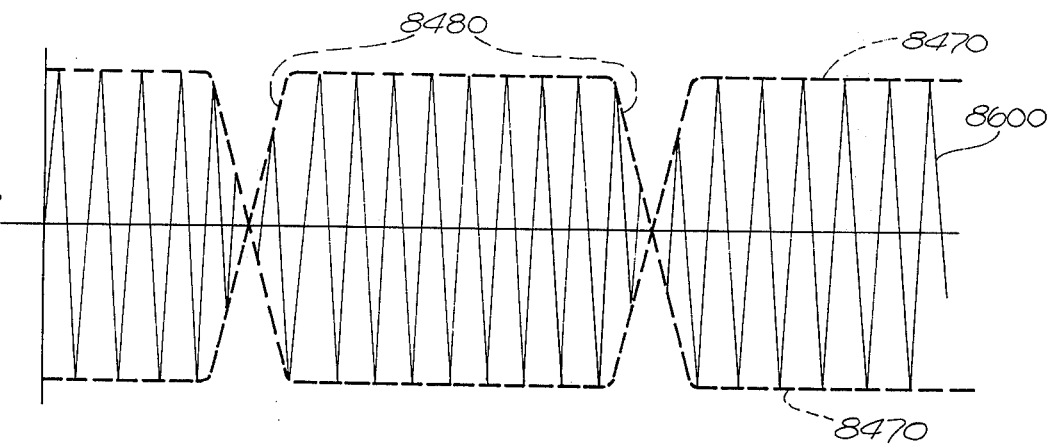

The envelope 8470 is again shown in FIG. 24 with a fundamental carrier 8600.

In FIG. 5, the outputs of dividers 302 and 303 are square waves. That is, they are perfectly square. The mark-to-space ratio is substantially equal to unity in each case. The frequency of one may or may not be slightly different from the other. The same is true of their pulse widths. However, the square wave amplitude in each case is the same.

It is well known that the Fourier analysis of a square wave yields $$y_o = \frac{4E_o}{\pi} \left( \cos x_o - \frac{1}{3} \cos 3x_o + \frac{1}{5} \cos 5x_o - \frac{1}{7} \cos 7x_o + \ldots \right) \quad (26)$$

where,
$x_o = 2\pi f_o t$,
$\pi = 3.14159$
$f_o$ is frequency, and
$t$ is time.

The Fourier analysis of the output of the air input circuit yields $$y_a = \frac{4E}{\pi} \left( \cos x - \frac{1}{3} \cos 3x + \ldots \right) \quad (27)$$

where,
$x = 2\pi f t$, and
$f$ is, for example, 314 Hz.

The Fourier analysis of the output of the gas input circuit yields $$y_g = \frac{4E}{\pi} \left( \cos kx - \frac{1}{3} \cos 3kx + \ldots \right) \quad (28)$$

where,
$k = 1 \pm \Delta$, and
$\Delta$ is in the range 0.003 to 0.01.

Using the trigonometric identify, $$\cos u + \cos v = 2 \cos \frac{u+v}{2} \cos \frac{u-v}{2} \quad (29)$$

$$y_a + y_g = \frac{8E}{\pi} \cos \frac{x+kx}{2} \cos \frac{\mp \Delta x}{2}$$

$$- \frac{1}{3} \cos \frac{3x+3kx}{2} \cos \frac{\mp 3\Delta x}{2}$$

$$+ \frac{1}{5} \cos \frac{5x + 5kx}{2} \cos \frac{\mp 5\Delta x}{2}$$

$$- \frac{1}{7} \cos \frac{7x + 7kx}{2} \cos \frac{\mp 7\Delta x}{2} + \ldots \quad (30)$$

Note that the driver coil may have an inductive reactance given by $$X_L = 2\pi f_m L \quad (31)$$

where $L$ is the inductance, and $$f_m = \frac{f + kf}{2}.$$

The term $f_m$ is the fundamental carrier. Note, $$\frac{x + kx}{2} = \frac{x(1 + k)}{2} = 2\pi f t \times \frac{1 + k}{2}$$

$$= 2\pi t \times \frac{f + kf}{2} \quad (32)$$

Note that the amplitude of the third harmonic is one-third that of the fundamental. However, the inductive reactance of the driver coil triples for the third harmonic, $3f_m$. Thus, the driver coil current may be, more or less, only about 11 percent of the fundamental amplitude. It is, thus, possible to use square waves rather than sine waves at the outputs of the input circuits without disturbing the resonant operation of the device as two combined electromechanical oscillators. Moreover, the circuit is more economical to construct because the square waves are used.

It is important to note two things:
1. There are no even harmonics.
2. All odd harmonics go to zero when the fundamental goes to zero.

This means that a sharp notch in the envelope is created. The notches are shown at 8480 in FIG. 24. The notches 8480 may be much deeper than as shown in FIG. 24. This provides for exceptionally good monitoring of the fundamental envelope frequency.

Not only do the terms cos 3x, cos 5x, etc., go to zero when cos $x = 0$, the terms cos 3 $x/2$, cos 5 $x/2$, etc., go to zero when cos $x/2 = 0$. That is, not only the odd harmonics all go to zero at the same time, their envelopes all go to zero at the same time as well.

THE DIGITAL COMPUTER 328 AND UTILIZATION MEANS 329 SHOWN IN FIG. 25

Figure 25:
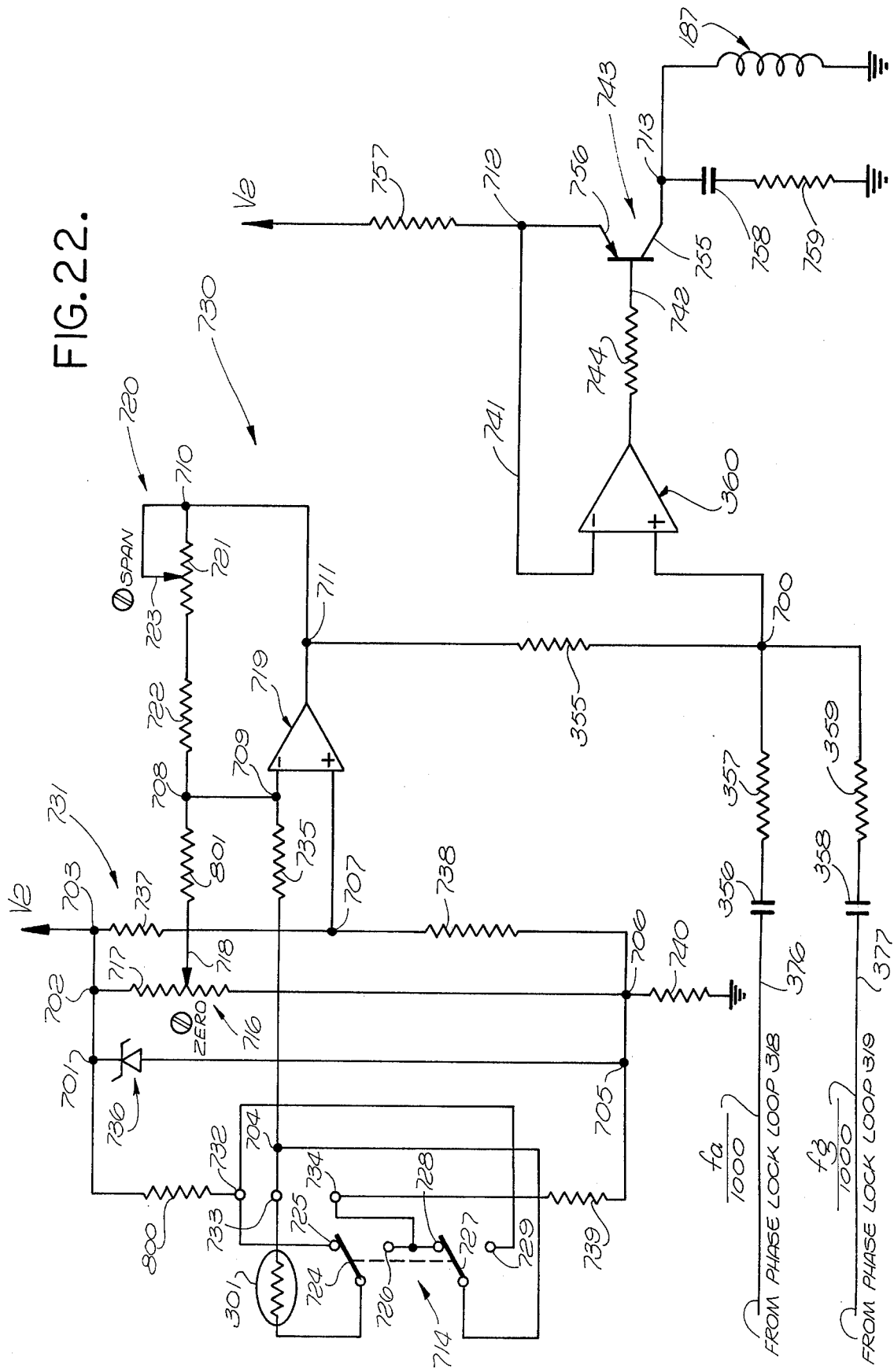
FIG. 25 is a detailed block diagram of a digital computer shown in FIG. 4.

Digital computer 328 shown in FIG. 4 is illustrated in greater detail in FIG. 25 wherein utilization means 329 is illustrated as an indicator 2700. Indicator 2700 is connected from a storage register 2600. In the alternative, if the gravitometer of the present invention illustrated in FIG. 4 is to be employed in the flowmeter of FIG. 1, indicator 2700 is removed, and the output of the gravitometer is connected to multiplier 36 through digital-to-analog converter 1001.

Leads 348 and 349 are illustrated in both of the FIGS. 4 and 25. A series of AND gates 380, 381, 382 and 383 are provided for inputs on leads 348 and 349, AND gates 381 and 382 also being connected from an output lead 384 of a 1 MHz. clock 385. Lead 348 is connected to one input of AND gate 380. Lead 349 is is connected to one input of AND gate 383. A cycle flip-flop 386 has a set input connected from an AND gate 3900, and a reset input connected from an AND gate 3600. Flip-flop 386 has a "1" output lead 387 and a "0" output lead 388. Lead 388 is connected to one input of AND gate 3900. Lead 387 is connected to one input of AND gate 3600.

Lead 387 is also connected to one input of each of AND gates 380 and 382. Lead 388 is also connected to one input of each of the AND gates 381 and 383.

An OR gate 389 is connected from the outputs of AND gates 380 and 381 to the input of a counter 390. An OR gate 391 is connected from the outputs of AND gates 382 and 383 to the input of a counter 392. Counter 392 has a capacity of 106 and resets on the millionth pulse input thereto via a lead 393 which is connected to counter 390, the reset input lead 394 of a flip-flop 395, its own reset lead 396 and to one input of each of AND gates 3900 and 3600.

In accordance with the foregoing, the reset pulse on the output lead 393 of counter 392 acts to reset most of the circuits illustrated in FIG. 25. At least most of the circuits that require resetting are reset by the reset pulse of counter 392. The outputs of AND gates 3900 and 3600 are connected to leads 397 and 398, respectively, the output pulses of AND gates 3900 and 3600 acting to reset and perform other functions.

The pulse impressed upon lead 397 via the output of AND gate 3900 serves to reset a counter 309, a rate multiplier 308 and a rate multiplier 1002. The pulse applied to lead 397 by AND gate 3900 also actuates a gating circuit 1006.

The pulse applied to lead 398 by AND gate 3600 is employed to operate a gating circuit 1004.

AND gates 399 and 400 are connected from counter 390 and produce output pulses on respective output leads 401 and 402 at predetermined counts of counter 390. These are impressed upon the set input of flip-flop 395 via an OR gate 403.

The "1" output of flip-flop 395 is connected to an output junction 404. Junction 404 is connected to one input of an AND gate 405 via a lead 406. Junction 404 is also connected to an input of an AND gate 407 via a lead 408.

AND gate 405 also receives another input over lead 409 connected to a junction 410, lead 348 also being connected to junction 410.

AND gate 407 also has another input lead 411 connected from clock 385.

The output of AND gate 405 is impressed on the counter 309 which temporarily stores a counted number of pulses while a second group of pulses are passed through rate multiplier 1002, the same being introduced to rate multiplier 1002 from the output of AND gate 407.

The output of rate multiplier 1002 is impressed upon rate multiplier 308 which multiplies a number manually set in a matrix 306 of switches 412.

The remainder of the structure of FIG. 25 not described hereinbefore and connected from a junction 413 over leads 414, 415 and 416 and the output of rate multiplier 308 may be entirely conventional. That is, the components and the combination thereof may be entirely conventional. Still further, each component part of the invention illustrated in FIG. 5, by itself, may be conventional. However, the combinations of the other structures thus far described are new.

The output of rate multiplier 308 is connected to a counter 2300 including a switch 3200, a logic circuit 1300, a storage register 1003 and an OR gate matrix 1005.

A switch matrix 307 and a gating circuit 1004 are connected in succession in that order to OR gate matrix 1005.

A gating circuit 1006, storage register 2600 and indicator 2700 are connected in succession in that order from storage register 1003.

OPERATION

In the operation of the embodiment of FIG. 25, a number is stored in counter 309 which is directly proportional to the difference between the gas period and a constant. A number of pulses are then run through rate multiplier 1002 from the output of AND gate 407 which is directly proportional to the reciprocal of the difference between the period of the air frequency and a constant.

Each pulse group which exits rate multiplier 1002 is then multiplied by a number adjustable with the switches 412 of switch matrix 306. The product of this constant times the ratio of the differences exits rate multiplier 308 and are counted in counter 2300. By virtue of the conventional operation of counter 2300, a number may be added or subtracted to the number of pulses in a group exiting rate multiplier 308 by the adjustment of switches 417 of switch matrix 307. The result is then indicated on indicator 2700. The indication may be binary or decimal or binary coded decimal (BCD).

It is old in the art to operate a counter such as counter 309 with a rate multiplier such as rate multiplier 1002 to perform a multiplication function. The same is true of switch matrix 306 and rate multiplier 308. Still further, each component and the combination thereof of the following components of FIG. 25 are old in the art: switch matrix 307, gating circuit 1004, OR gate matrix 1005, logic circuit 1300, storage register 1003, gating circuit 1006, storage register 2600 and indicator 2700.

Figure 26:
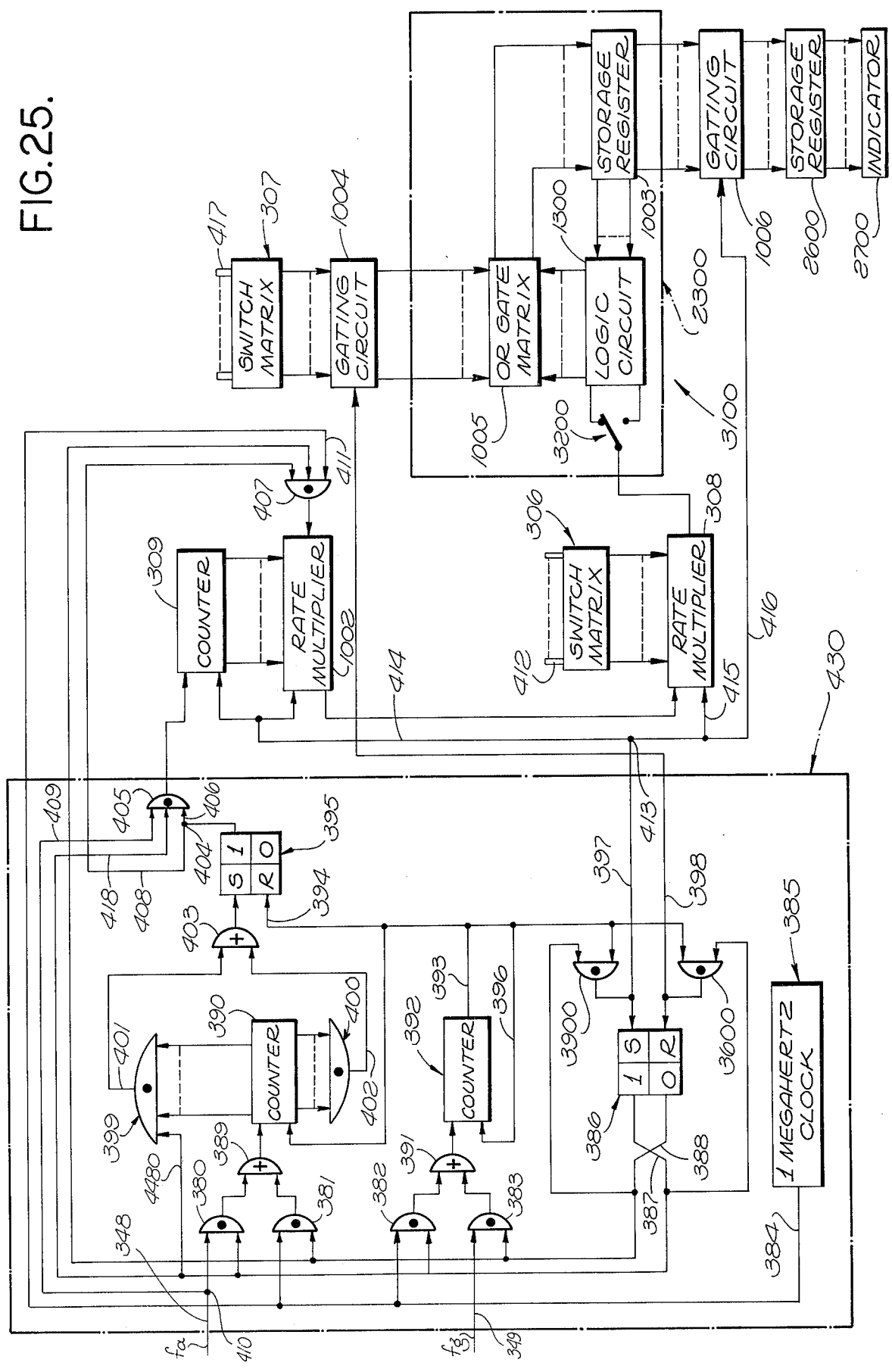
FIG. 26 is a graph of a group of waveforms illustrating the operation of the computer of FIG. 25.

In FIG. 26, the approximate reciprocal calculation period is P1. The calculation of the difference period is P2. Typically, P1 is 1.0 second and P2 is 3.2 seconds.

Pulses are indicated having widths P3 and P4. The widths of pulses P3 and P4 have been greatly exaggerated for clarity. Pulses P3 and P4 are comparatively much smaller than as illustrated. Pulse P3 has a width which is typically about 2/314 of the period P1. The width of P4 is similarly typically about 2/321 of the period P2.

Period P1 is determined by how long the "1" output of flip-flop 386 in FIG. 25 is high.

When counter 392 in FIG. 25 is counting the clock pulses, counter 390 is counting the air pulses via gates 382 and 380, respectively. On a fixed constant count, the calculation of which will be explained hereinafter, AND gate 399 sets flip-flop 395. Flip-flop 395 then opens AND gate 405 and loads counter 309 with air pulses until flip-flop 395 is reset by counter 392. Lead 418 is connected from lead 387 to insure that counter 309 only counts during period P1. Waveform 419 in FIG. 28 shows the "1" output of flip-flop 386.

Pulses P3 and P4 are generated at the "1" output of flip-flop 395.

During period P2, counter 390 counts the clock, and counter 392 counts the gas frequency. AND gate 400 then produces a pulse before counter 392 resets and sets flip-flop 395 so that it produces a pulse P4.

The output of AND gate 405 is, thus, a pulse group having a period P3 of a frequency $f_a$, and the output of AND gate 407 is a group of pulses of the clock frequency which extend over the period P4.

Typically, counter 390 is a long counter and counts perhaps a little more than 3,200,000 pulses before counter 392 resets it. The reason for this is that it is difficult and sometimes impossible to obtain highly accurate, very high frequency sources. The problem is that in order to solve the gravity equation, a very short time and/or a very high frequency must be very accurately measured.

Groups of pulses are illustrated at 421, 422, 420 and 423 in FIG. 26 having locations corresponding to pulses P3, P4 and other pulses, respectively. The pulses in groups 420 and 422 are of a 1 MHz. frequency. The pulses in groups 421 and 423 are of the $f_a$ frequency.

Counter 309 in FIG. 25 and rate multiplier 1002 therein then multiply, for example, the number of pulses of group 421 by the number of pulses of group 422.

The purpose of the remainder of the structures illustrated in FIG. 25 mainly is for calibration, normalization, and readout. However, as will be explained, factory calibration may be somewhat more complicated. For this reason, switch matrices 306 and 307 may or may not be employed for span and zero corrections for field calibration, as desired. These and other structures may sometimes be omitted. However, switch matrix 306 and rate multiplier 308 or some other structure is required for calibration.

With the structures shown in FIG. 25, the decimal equivalent of gravity may be read directly from indicator 2700 is conventional strucutres are used.

Counter 309 preferably has a capacity of counting 2,000 to 3,000 pulses. Preferably, a number of pulses are run through rate multiplier 1002 which is slightly more than ten times the maximum number expected to be stored in counter 309, as is conventional for binary coded decimal (BCD) operation.

Throughout this description, reference will be made to the text of certain U.S. patents and U.S. patent applications. These patents and patent applications are listed for convenience forthwith.

Reference is hereby made to the following patents:
1. U.S. Pat. No. 3,677,067.
2. U.S. Pat. No. 3,706,220.
3. U.S. Pat. No. 3,738,155.
4. U.S. Pat. No. 3,741,000.
5. U.S. Pat. No. 3,783,259.

The foregoing patents of paragraphs (1), (2), (3), (4) and (5) are hereinafter referred to as patents P1, P2, P3, P4 and P5, respectively.

Reference is hereby made to the following U.S. patent applications:
1. U.S. patent application Ser. No. 265,327 filed June 22, 1972, for METHOD OF AND APPARATUS FOR PRODUCING ANALOGS AND FLOWMETERS INCORPORATING GRAVITOMETERS by G. L. Schlatter and C. E. Miller.
(2) U.S. patent application Ser. No. 321,662 filed Jan. 8, 1973, for PULSE TRAIN MODIFICATION CIRCUIT by P. Z. Kalotay and G. A. Fitzpatrick.

The foregoing U.S. patent applications (1) and (2) are referred to hereinafter as applications L1 and L2, respectively.

An off-set digital computer 3100 in FIG. 25 receives an input from rate multiplier 1002 and from the outputs of AND gates 3600 and 3900.

An indicator 2700 is connected from the output of off-set digital computer 3100. Off-set digital computer 3100 may be decimal or binary. The indicator 2700 may be a simple indicator with one lamp for each binary stage or a decimal indicator. Indicator 2700 may be entirely conventional. Off-set digital computer 3100 may be entirely conventional or any of the types disclosed in copending application Ser. No. 423,409 filed Dec. 10, 1973, for DENSITOMETER by G. L. Schlatter, and assigned to the assignee of this application. The entire contents of said copending applications L1, L2 and Ser. No. 423,409 are incorporated herein hereat by this reference hereto.

Off-set computer 3100 in FIG. 25 produces a binary or a binary coded decimal (BCD) output so that indicator 2700 may be read directly, binary or decimal, in specific gravity G, where $$G = KN_a + B \qquad (33)$$

and $K$ is the setting of switch matrix 306, $N_a$ is the number of rate multiplier 1002 output pulses in a group.

The constant B is the setting of switch matrix 307. The constant B may be zero after factory calibration. The constants K and B are employed for convenience in field calibration. The constant B apparatus may be eliminated in some cases.

The constant B may be positive or negative. The position of a switch 3200 in FIG. 25 determines whether a counter 2300 counts up (B positive) or down (B negative).

A main storage register 1003 is illustrated in FIG. 25. As will be described, a predetermined number B is entered in storage register 1003 periodically.

A logic circuit is provided at 1300. Logic circuit 1300 has an input from rate multiplier 308 through switch 3200.

In FIG. 25, the said predetermined number B is periodically entered in storage register 1003. The magnitude of the predetermined number B may be selected or changed by operating binary or binary coded decimal (BCD) switches which are located in a switch matrix 307. The switches in matrix 307 are either connected from a positive potential or ground. The outputs of the switches are sampled and impressed upon storage register 1003 periodically. A gating pulse is impressed upon a gating circuit 1004 for this purpose.

Gating circuit 1004 is connected from matrix 307 to an OR gate matrix 1005. The output of OR gate matrix 1005 is then impressed upon storage register 1003.

Once the said predetermined number B has been entered into storage register 1003, logic circuit 1300 then controls the register 1003 to count up or down depending upon whether the algebraic sign of B, switch 3200 in FIG. 25 being placed in the one or the other corresponding positions thereof, respectively, on this account. The output of logic circuit 1300 is, thus, impressed upon storage register 1003 through OR gate matrix 1005. Logic circuit 1300 receives pulses to count from switch 3200. Logic circuit 1300 receives other inputs from storage register 1003.

From the foregoing, it will be appreciated that matrix 1005 with logic circuit 1300 and storage register 1003 form either a count up counter or a count down counter depending upon in which position switch 3200 lies. This counter may be entirely conventional, if desired.

The output of storage register 1003 is also sampled periodically by a gating circuit 1006 which may be of the same type as gating circuit 1004. Gating circuit 1006 receives pulses from AND gate 3900 in FIG. 25 to cause it to sample the output of register 1003. The output of gating circuit 1006 is impressed upon a storage register 2600. The output of the storage register 2600 is impressed upon indicator 2700.

If desired, indicator 2700 may be a binary indicator or a BCD indicator.

All of the structures 1003, 1300, 307, 1004, 1005, 1006, 2600 and 2700 may be entirely conventional or may or may not be identical to the corresponding structures disclosed in U.S. Pat. No. 3,775,597.

Alternatively, indicator 2700 may simply be a row of lamps each connected from the "1" output of each of the flip-flops in storage register 2600.

Pulses are supplied from AND gate 3600 to gating circuit 1004.

The purpose of the switch matrix 307 is to set, periodically, the flip-flops in storage register 1003 to selected states.

Switch matrix 307 may have one double-pole, double-throw switch for each bit or flip-flop in register 1003. Gating circuit 1004 may have an AND gate for the set "1" and set "0" inputs to each bit or flip-flop in register 1003. The OR gate matrix 1005 may have an OR gate for the set "1" and set "0" inputs of each bit in register 1003.

The same outputs of the bits in register 1003 are connected both to logic circuit 1300 and to gating circuit 1006.

Although a symbol has been used consistently in the drawings to represent OR gates, it is to be understood that the symbol includes, but is not limited to, a wire OR gate. Thus, one or more or all of the symbols employed herein to represent an OR gate may or may not be a wire OR gate, as desired.

The phrase "AND gate," as used herein and as used in the claims, is hereby defined to include a NAND gate with or without an inverter, and vice versa.

The phrase "OR gate," as used herein and as used in the claims, is hereby defined to include a NOR gate with or without an inverter, and vice versa.

All of the said patents P1, P2, P3, P4 and P5 are hereby incorporated herein by this reference hereto as though fully set forth herein hereat.

The said L1 application is, by this reference hereto, hereby incorporated herein as though fully set forth herein hereat.

Indicator 2700 may be entirely conventional. For example, it also may be one sold by the Burroughs Corporation under the trademark PLANAPLEX.

Rate multipliers 1002 and 308 may be entirely conventional. Any one including, but not limited to, those sold by Motorola Semi-conductor Products, Inc. and Texas Instruments Incorporated may be employed. The Motorola model numbers are MC 14527AL and MC 14527CL. The Texas Instruments rate multipliers are described as synchronous rate multipliers with circuit types SN7497 and SN74167. The foregoing Motorola and Texas Instruments model numbers are generally given for what is described herein as a "rate multiplier decade" which may be connected seriatim ad infinitum, if desired.

Off-set digital computer 3100 shown in FIG. 25 may be entirely conventional. One or many such computers may be employed. One such computer is sold as an MOS by Hughes Aircraft Company. This MOS is described further as a counter/latch/decoder/driver

HCTRO107D/HCTRO107F.

Alternatively, a portion of or all of the digital structures disclosed herein may be BCD or binary.

The theory of operation of the embodiment of FIG. 25 is as follows. Computation of gravity G is made in accordance with the formula $$G = [K'] [f] \left[\frac{T_g}{10^{-6}} - \frac{T_{go}}{10^{-6}}\right] [f_a] \left[T - \frac{Tf_{ao}'}{f_a}\right] \quad (34)$$

where, $K'$ is a constant,
$T_{go}$ is the gas vacuum period,
$f_{ao}'$ is a constant,
$f$ is the constant pulse repetition frequency (PRF) of the output signal (e.g. square wave—mark-to-space ratio unity) of clock 385 (e.g. 1.0 MHz.),
$T$ is a constant period (e.g. 1.0 second),
$f_a$ is the PRF of the input signal applied over lead 348 to the input of each of the AND gates 380 and 405, and $$T_g = \frac{1}{f_g} \quad (35)$$

where, $f_g$ is the PRF of the input signal applied to the input of AND gate 383 over lead 349.

Each pulse group output of rate multiplier 1002 is equal to G/K'. When the embodiment of FIG. 25 is fully calibrated except for K', the gas of a known gravity is passed through the gas chamber, and switches 412 are operated until indicator 2700 shows the said known gravity. Normally, but not as an absolute necessity, nothing is added to or subtracted from each pulse group output of rate multiplier 308 in this factory calibration and switches 417 are all normally, but not necessarily, set to zero.

During the high "1" output of flip-flop 386, gate 382 is opened to admit clock pulses to $10^6$ counter 392 which counts the 1 megahertz clock frequency forming the period T equal to exactly 1 second.

At the same time that counter 392 counts the clock pulses, counter 390 counts the pulses $f_a$. Gate 399 is set to produce an output pulse when the count of counter 390 is $f_{ao}$. In this case, gate 399 sets flip-flop 395 which opens gate 405 and allows it to dump the balance of the $f_a$ pulses into counter 309 provided that (as assumed previously—the "1" output of flip-flop 386 is high. Note that AND gate 405 has input leads from three signal sources, viz. $f_a$ lead 348, flip-flop "1" output lead 387 and lead 406 connected from the "1" output of flip-flop 395.

In accordance with the foregoing, and in this case, the pulse from the "1" output of flip-flop 395 has a time width $$\left[T - \frac{Tf_{ao}'}{f_a}\right] \quad (36)$$

where, $T$ may be 1.0, and
$$f_{ao}'/f_a \quad (37)$$
is the period (T = 1.0) between the start of the $f$ and $f_a$ counts by counters 392 and 390, respectively, and the output pulse of gate 399. Notice that the reset output lead 393 of counter 392 is connected to the reset input of flip-flop 395 terminate the "1" output pulse thereof at the end of the one second time interval.

The number of pulses in any single group exiting AND gate 405 is then equal to $$[f_a] \left[T - \frac{Tf_{ao}'}{f_a}\right] \quad (38)$$

because $f_a$ pulses pass AND gate 405 for the period (36).

The product of (38) and (39) (combination of counter 309 and rate multiplier 1002), thus, gives G/K' which is converted to G by the calibration procedure described previously.

$$[f] \left[\frac{T_g}{10^{-6}} - \frac{T_{go}}{10^{-6}}\right] \quad (39)$$

Product (39) is obtained when flip-flop 386 is reset and the "0" output thereof is high. In this case, counter 392 is fed with $f_g$ pulses to arrive at
$T_g/10^{-6}$
or $\quad (40)$
$T_g \times 10^6$ The clock pulses are simultaneously fed to counter 390 which has AND gate 400 that produces an output pulse on the count of $T_{go} \times 10^6$. Because flip-flop 395 is set on this count and reset at $T_g \times 10^6$, the time width of the "1" output of flip-flop 395 in this case is $$[T_g - T_{go}] [10^6] \quad (41)$$

Making sure that the "0" output of flip-flop 386 is high by a connection from lead 388 thereof to AND gate 407, AND gate 407 passes clock pulses for the duration of the period (41). Note that AND gate 407 has connections from three leads, viz. output lead 384 of clock 385, the "0" output lead 388 of flip-flop 386 and lead 408 connected from the "1" output of flip-flop 395.

The number of pulses in any group at the output of AND gate 407 is then equal to $$[f] [T_g - T_{go}] [10^6] \quad (42)$$

Note that the product of (38) and (39) performed by counter 309 and rate multiplier 1002 is equal to G/K', and that (39) is equal to (42).

Equation (34) may be simplified to
$$G = K (T_g - T_{go}) (f_a - f_{ao}') \quad (43)$$
where, $$K = \frac{K'fT}{10^{-6}} \quad (44)$$

The term $T_{ao}$ will not necessarily and maybe never be equal to the reciprocal of $f_{ao}$ for the best corresponding mechanizations of both of the equation (43). The terms of equation (43) are not the result of rigorous mathematical analysis, but a gravity output in accordance therewith is strikingly accurate and to not only an extraordinary, but to an astonishing degree.

The gravitometer of the present invention mechanized as in equation (34) is calibrated as follows.

Draw a vacuum (small density in comparison to density to be measured) on the gas vane chamber and measure the frequency or period of the wave appearing at junction 327 in FIG. 4. This frequency is called the gas vacuum frequency. If the frequency is measured, calculate the period by calculating the reciprocal of the frequency. Preferably, all measurements should be accurate to six or more decimal places. The period of the gas vacuum frequency is the gas vacuum period and is $T_{go}$. Set AND gate 400 to produce an output pulse on the count of $T_{go} \times 10^6$.

Measure, or measure and then calculate, the frequencies $f_m$ and $f_n$ or respective periods $T_m$ and $T_n$ of the wave appearing at junction 325 in FIG. 4 with one gas at two different known densities $d_m$ and $d_n$. Alternatively, two different gases of two known, but different, densities $d_m$ and $d_n$ may be employed. However, a single gas may be employed at different pressures and/or temperatures so long as $d_m \neq d_n$.

Use the formula
$$d = C (f_a - f_{ao}) \qquad (45)$$
where, $d$ is air density, and $C$ is a constant.

Solve (46) and (47) simultaneously for $C$ and $f_{ao}''$
$$d_m = -C (f_m - f_{ao}'') \qquad (46)$$
$$d_n = -C (f_n - f_{ao}'') \qquad (47)$$
Thus, $$f_{ao}'' = \frac{d_m f_n - d_n f_m}{d_m - d_n} \qquad (48)$$

and $$C = \frac{-d_m + d}{f_m - f_n} \qquad (49)$$

Then find $f_{ao}'$ as follows:

$$f_{ao}' = \frac{2d_c + Cf_{ao}''}{C} \qquad (50)$$

Set AND gate 399 to produce an output pulse on the count of $f_{ao}'$ given by (50).

There are two alternative methods of computation that may give exactly the same and sometimes, or always at least a slightly more accurate value for $f_{ao}'$. These follow.
$$d = C(T_a - T_{ao}) \qquad (51)$$
Find $$T_{ao} = \frac{d_m T_n - d_n T_m}{d_m - d_n} \qquad (52)$$

$$C = \frac{d_m - d_n}{T_m - T_n} \qquad (53)$$

$$T_{ao}'' = \frac{2d_c + CT_{ao}}{C} \qquad (54)$$

$$f_{ao}' = \frac{1}{T_{ao}''} \qquad (55)$$

The third alternative is to draw a vacuum on the air chamber to obtain air vacuum period $T_{ao}$. Then find C in (51) using one gas of known density $d_p$ at which the air vane period is $T_p$.

Again, compute C $$C = \frac{d_p}{T_p - T_{ao}} \qquad (56)$$

The approximation error is then zero at air frequency $f_c$ when $$f_{ao}' = \frac{f_c^2}{f_{ao}} \qquad (57)$$

If desired, $$f_c = \frac{C}{d_c + CT_{ao}} \qquad (58)$$

where $C$ is as defined in (56).

It is to be noted that each counter or other component which is reset may have added an override, if desired or necessary. Such an override may be added external or internal. Such an override is illustrated in FIG. 27 where a counter 451 is shown having an input lead 452 connected thereto through an AND gate 453. A reset input lead is shown at 454 connected to a junction 455. An inverter 456 is connected from junction 455 to a second input of AND gate 453. The conventional reset input lead of counter 451 is shown at 457 connected from junction 455.

THE ALTERNATIVE EMBODIMENT OF FIG. 28

In the embodiment of FIG. 28, switch matrix 306 and rate multiplier 308 are duplicated from FIG. 25. To form the embodiment of FIG. 28, all of the structures shown in FIG. 28 would be added to all those shown in FIG. 25 except switch matrix 306, rate multiplier 308, switch matrix 307, gating circuit 1004, counter 2300, gating circuit 1006, storage register 2600 and indicator 2700. Counter 2300 would be replaced by a counter 23000 in FIG. 28. Counter 23000 may be identical to counter 2300 except that AND gates 459 and 460 are employed in FIG. 28 to perform the same function as switch 3200 in FIG. 25.

The embodiment of FIG. 28 may, for example, employ a counter 461 to divide $f_g$ by two times the gas vacuum frequency. A counter 462 may be employed to divide the air frequency by two times the air vacuum frequency.

Counter 461 has an output lead 463 upon which a pulse is impressed thereby when the counter 461 has counted $2f_{go}$ pulses. Counter 462 has an output lead 464 upon which is impressed a pulse when the counter 462 counts the pulse $2f_{ao}$. The pulses on leads 463 and 464 set flip-flops 465 and 466, respectively.

The "1" output of flip-flop 466 is connected to the inputs of AND gates 467 and 469. The "0" output of flip-flop 466 is connected to the input of AND gate 470. The "1" output of flip-flop 465 is connected to AND gates 469 and 470. The "0" output of flip-flop 465 is connected to AND gate 467.

The 1 MHz. clock 472 is connected to the inputs of AND gates 469 and 471. The outputs of AND gates 467 and 470 are connected to respective inputs of an OR gate 473, the output of which is passed through AND gate 471 and rate multiplier 308 to one input of each of AND gates 459 and 460.

AND gate 459 receives another input from the output of AND gate 467. AND gate 460 receives another input from the output of AND gate 470.

OPERATION

AND gate 467 produces an output pulse when flip-flop 466 is set before flip-flop 465 is set. The number of these pulses then passed by AND gate 471 is determined by the width of the output pulse of AND gate 467. The number of these pulses is directly proportional to the difference between a normalized gas period and a normalized air period. The converse is true relative to AND gate 470.

AND gate 469 is the reset gate which resets by the clock when the "1" output of each of the flip-flops 465 and 466 are high. Counters 461 and 462 are reset at the same time as flip-flops 465 and 466 are reset.

In FIG. 28, the gravity computation is made thus:

$$G = K \left( \frac{T_g}{T_{go}} - \frac{T_a}{T_{ao}} \right) + B \qquad (59)$$

The constants $K$ and $B$ are determined by solving two simultaneous equations knowing two gravities, two respective periods $T_g$, two respective periods $T_a$, and measuring $T_{go}$ and $T_{ao}$ during evacuation of each of the respective gas and air chambers.

The constant K is the setting of switch matrix 306 in FIG. 25, as before. The constant B is the setting of switch matrix 307 in FIG. 25.

Counter 462 is set to count $f_{ao}$. The counter 461 is set to count $f_{go}$. On the count of $f_{ao}$, counter 462 sets flip-flop 466. From reset by AND gate 469 to count $f_{ao}$ is the period $$T_a/T_{ao} \qquad (60)$$

Similarly, from reset to the set of flip-flop 465 is the period $$T_g/T_{go} \qquad (61)$$

The logic of gate 467 is such that it produces an output pulse only when $$T_g/T_{go} \qquad (62)$$

is larger than $$T_a/T_{ao} \qquad (63)$$

Thus, from (59), counter 23000 counts up. Note that clock 472 supplies pulses during the period of the output pulse of gate 467 through AND gate 471 and rate multiplier 308 to the "count up" input of reversible counter 23000 through AND gate 459. Note that AND gate 459 has a second input from the output of AND gate 467 to gate AND gate 459 on.

When AND gate 467 produces an output pulse, AND gate 470 does not, and vice versa.

The converse of all that has been said since (59) is also true.

When flip-flop 465 is set before flip-flop 466 is set, only AND gate 470 and no AND gate 467 produces an output pulse which gates the clock only to the "count down" input of counter 23000.

Reset by AND gate 469 occurs only on the first clock pulse after the "1" output of each of the flip-flops 465 and 466 is high. For better stability if desired, AND gate 469 may or may not have the input leads thereto from flip-flops 465 and 466 replaced with delay devices each having a delay at least slightly more than the maximum expected value of $T_g/2$ or $T_a/2$, whichever is larger, and connected from each "1" output of each respective flip-flop 465 and 466.

Orifice 312 in FIG. 4 provides a substantially constant flow rate of the sample gas.

In the prior art, gravitometers have had, for example, a 45 minute time constant. The gravitometer of the present invention more accurately follows and has a superior dynamic response in that gravity calculated every 4 seconds or in less than 1.7 seconds.

From the foregoing, it will be apparent that all of the systems herein may be binary, or all of them may be binary coded decimal (BCD), or one or more or all of the systems may be part binary and part BCD.

Differentiators and/or one-shots may or may not be added or deleted in any system disclosed herein, as desired.

From the foregoing, it will also be apparent that the signals appearing at junctions 324, 325, 326 and 327 in FIG. 4 are all square waves similar to the square waves illustrated at 7300 and 7320 in FIG. 23.

The phrase "AND gate" is hereby defined to include a NAND gate with or without an inverter.

The phrase "NAND gate" is hereby defined to include an AND gate with or without an inverter.

The word "gravitometer" is hereby defined to include any instrument which produces an output directly proportional to the ratio of the density of two fluids.

The word "fluid" is hereby defined to mean a gas or liquid, when applicable.

The word "gravitometer" is not necessarily limited to an instrument for producing an output directly proportional to the density of a sample gas to air or the data of a sample liquid to water, or the density of a sample fluid, liquid or gas, to any reference fluid, liquid or gas.

The word "gravitometer" is hereby defined for use herein and for use in the claims as are the other definitions herein, as a device for producing either an analog or digital output directly proportional to gravity with or without utilization means including, but not limited to, a voltmeter calibrated in density, a process controller, a flowmeter, a digital indicator or any other device or system.

The word "gravity" is hereby defined for use herein and for use in the claims as the output of a gravitometer and is not limited in definition any more than the word "gravitometer" is limited by the definitions herein. Moreover, the word "gravity" is as broad as the broadest definition of "gravitometer" herein.

The phrase "rate multiplier" is hereby defined for use herein and for use in claims to mean a counter of any radix including, but not limited to, a binary coded decimal (BCD) or decimal counter having one or preferably four stages or decades resetting on the ten thousandth count.

All the definitions set forth hereinbefore and hereinafter are for use herein and for use in the claims.

The phrase "rate multiplier" is hereby defined to include, but not be limited to, all the stages or decades in any BCD or decimal counter employing more than one stage or decade.

In FIG. 4, low pass filter 321 and low pass filter 3210 may be identical. One or both or neither may or may not have a cut-off frequency below the second harmonic of the output signals of the outputs of phase detectors 320 and 3200 but may conveniently be so constructed with a cut-off frequency below the said second harmonic and above the fundamental, which is, in the cases of phase detectors 320 and 3200, perhaps midway between 300 and 400 Hz.

In FIG. 4, each of the phase detectors 320 and 3200 may be conventional or may be four quadrant analog multipliers. See Neil Marshall, U.S. Pat. No. 3,783,259.

The clocks disclosed herein may include crystal controlled oscillators which produce square wave output signals with or without the use of internal or external squarers.

Figure 29:
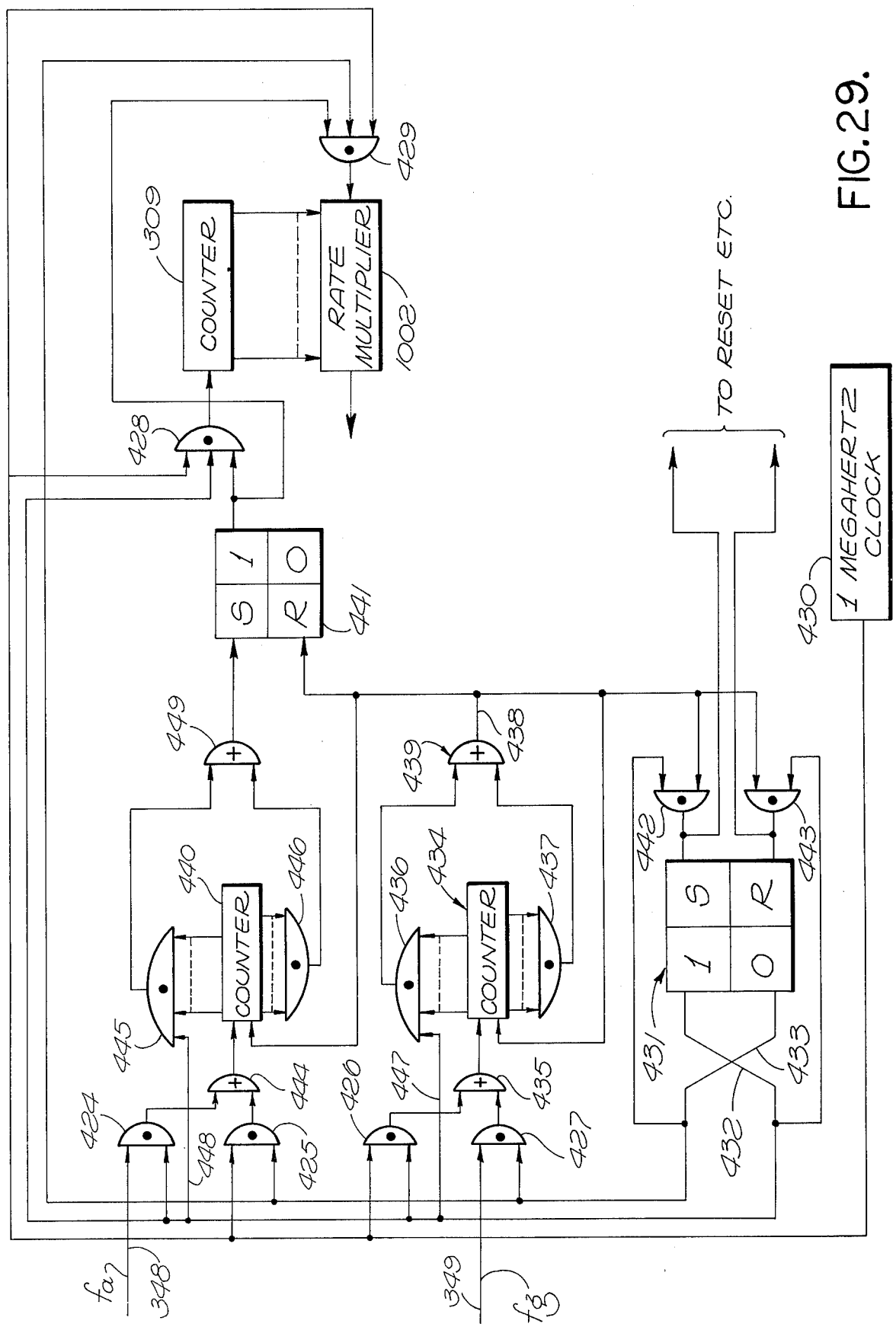

In FIG. 29, AND gates 424, 425, 426 and 427 are provided, as before. However, these AND gates are reconnected in a different way. The same is true of AND gates 428 and 429. All the structures in FIG. 29 may be substituted for that illustrated in the dotted box 430 shown in FIG. 25 except that counter 309 and rate multiplier 1002 are illustrated in FIG. 25. The same is true of leads 348 and 349.

Lead 348 is connected to one input of AND gate 424 in FIG. 29. Lead 349 is connected to one input of AND gate 427. A 1 MHz. clock 430 is again provided and connected to one input of each of the AND gates 425 and 426. A flip-flop 431 is provided with a "1" output lead 432 and a "0" output lead 433.

The "1" output lead 432 is connected to AND gates 424 and 426. "0" output lead 433 is connected to AND gates 425 and 427.

A cycle counter 434 receives the output of AND gates 426 and 427 via an OR gate 435. Counter 434 has AND gates 436 and 437 connected therefrom to produce output pulses at different predetermined counts. Further, AND gate 436 is connected from the "1" output lead 432 of flip-flop 431 and does not produce an output pulse unless the "1" output of flip-flop 431 is high.

A reset pulse appears upon an output lead 438 of an OR gate 439 that resets counter 434 as before, and also resets a counter 440, a flip-flop 441 and changes the state of flip-flop 431 in the conventional way via AND gates 442 and 443.

The outputs of AND gates 436 and 437 are connected to respective inputs to OR gate 439.

The outputs of AND gates 424 and 425 are passed to counter 440 via an OR gate 444. Counter 440 has two AND gates 445 and 446 which produce output pulses at predetermined different respective counts. However, AND gate 445 cannot produce an output pulse unless the "1" output of flip-flop 331 is high because of a connection from lead 432. Such connections for AND gates 436 and 445 are indicated at 447 and 448, respectively. A similar connection 4480 is provided in FIG. 25. The reason for this is that only the "1" output of flip-flop 441 in FIG. 29 is employed to produce pulses P3 and P4 in FIG. 26 and it is desirable to produce an output from gates 436 and 445 only on alternate "half cycles" and not on each "half cycle" because different computations are made during any two immediately adjacent "half cycles." For convenience only, reference is made throughout this specification to period P1 in FIG. 26 as being a "half cycle" and to period P2 being a "half cycle," even though P1 ≠ P2.

The outputs of AND gates 445 and 446 are employed to set flip-flop 441 through an OR gate 449. As before, each of the AND gates 428 and 429 receives three inputs. Each of the AND gates 428 and 429 receive one input from the "1" output of flip-flop 441. AND gate 428 receives another input from the "1" output of flip-flop 431. Still further, both of the AND gates 428 and 429 receive clock pulses which is one of several differences from the embodiment of FIG. 25 which allows a data period reduction of from about 4.2 seconds to about 3.3 seconds. A different method of computation is used, as will be described.

Counter 434 still can count 1 million pulses. However, AND gate 436 produces an output at a count of slightly over 300,000 which, with the output of gate 445, causes the "1" output of flip-flop 441 to be high for only 0.002 second, or thereabouts. At this time, the clock pulses are entered in counter 309 through AND gate 428. The other computation "half cycle" or interval is the same as in FIG. 25. Counter 440 counts perhaps slightly above 3.2 million pulses and somewhat in excess of 20,000 pulses are passed through rate multiplier 1002 from the output of AND gate 429.

In FIG. 29, the computation of gravity is performed by the equation $$G = K(T_a - T_{ao})(T_{ao}' - T_a) \qquad (64)$$

where $T_{go}$ is the gas vacuum frequency measured as before, and $$T_{ao}' = 2T_c - T_{ao} \qquad (65)$$

where, $T_c$ is the air period at density $d_c$, and $T_{ao}$ is the air vacuum period measured as before.

Counter 309 requires only one-tenth the number of pulses that rate multiplier 1002 does. When the $f_a$ pulses are fed to counter 440, clock pulses are fed to counter 434 at the same time. Gate 445 later produces an output at $T_a \times 10^5$ second from reset (slightly more than $T_{ao}' \times 10^5$). Gate 436 produces an output pulse at $T_{ao}' \times 10^5$ second from reset (about 0.32 second). The clock pulses are then fed to counter 309 from time $T_{ao}' \times 10^5$ to time $T_a \times 10^5$ (about 2,000 pulses at density $d_c$).

The pulses to rate multiplier 1002 are supplied in exactly the same way as in FIG. 25.

Alternatively, the $(T_g - T_{go})$ clock pulses may be fed to counter 309 reduced from $\times 10^6$ to $\times 10^5$ and the $(T_{ao}' - T_a)$ clock pulses may be fed to rate multiplier 1002 increased in number from $\times 10^5$ to $\times 10^6$.

THE ALTERNATIVE EMBODIMENT OF FIG. 30

Figure 30:
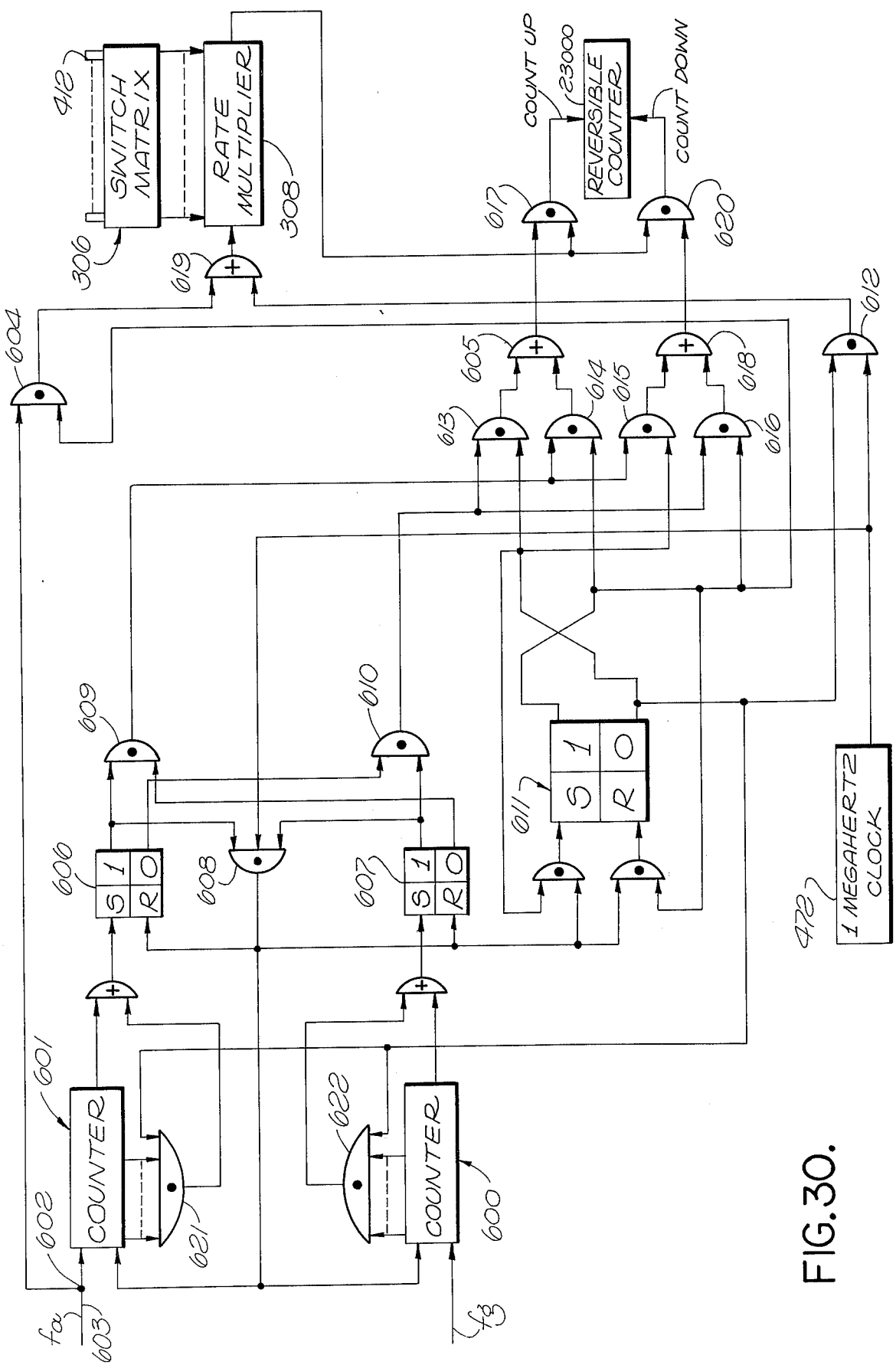

The embodiment of FIG. 30 is similar to the embodiment of FIG. 28 but somewhat more accurate. Counters are provided at 600 and 601 in FIG. 30 which may be identical to counters 461 and 462 shown in FIG. 28.

One addition in FIG. 30 is a junction 602 connected from an input lead 603 carrying $f_a$ pulses. An AND gate 604 receives an input from junction 602 as well as counter 601. AND gate 604 also receives an input from an output of OR gate 605. Flip-flops 606 and 607 may be identical to flip-flops 466 and 465, respectively, in FIG. 28.

An AND gate 608 is provided in FIG. 30 which may be identical to AND gate 469 in FIG. 28.

Other AND gates 609 and 610 are provided in FIG. 30 which may be identical to AND gates 467 and 470 in FIG. 28.

In FIG. 30, a flip-flop 611 changes state each cycle and is set and reset alternately by the output reset pulses of AND gate 608.

From previous discussions, it will be apparent that AND gate 609 produces an output pulse when the gas period exceeds the air period. Conversely, AND gate 610 produces an output pulse when the air period exceeds the gas period. As will be explained, a moderate improvement in accuracy is achieved from the use of the embodiment of FIG. 30 over the embodiment of FIG. 28. This involves the use of $f_a$ pulses to the "1" input of gate 604 alternately with the input of clock pulses to an AND gate 612. Which of the AND gates 604 and 612 should produce output pulses depends upon four conditions. Which way reversible counter 23000 should count also depends upon the same four conditions. These four conditions are detected by AND gate 613, 614, 615 and 616. OR gate 605 produces an output pulse when gate 609 produces an output pulse and the "1" output of flip-flop 611 is high, or the "0" output of flip-flop 611 is high, and AND gate 610 produces an output pulse. This means that $f_a$ pulses should be passed through rate multiplier 308, and reversible counter 23000 set to count up. That is the purpose of AND gates 604 and 617, respectively.

An OR gate 618 produces an output pulse either when a pulse is produced at the output of AND gate 609 and the "0" output of flip-flop 611 is high, or an output pulse is produced from AND gate 610 and the "1" output of flip-flop 611 is high.

The connections from OR gate 605 operate AND gates 604 and 617. The output of OR gates 618 operates AND gate 612 corresponding to AND gate 604 to admit clock pulses to an OR gate 619, the same being adapted to admit output pulses of AND gate 604 to rate multiplier 308 as well as the clock pulses produced at the output of AND gate 612. In this case, counter 23000 counts down because of a connection to AND gate 620 from the output of OR gate 618.

Clock 472 is provided, as before.

The computer of FIG. 30 produces an output signal directly proportional to G where $$G = K \left( \frac{T_g}{T_{go}} - \frac{T_a}{T_{ao}} \right) \left( f_a - f_{ao}' \right) + B \tag{66}$$

$$f_a \left( \frac{T_g}{T_{go}} - \frac{T_a}{T_{ao}} \right) \tag{67}$$

is computed on alternate half cycles because of the cycle of flip-flop 611.

$$f \left( \frac{T_g \times f_{ao}'}{T_{go} \times 10^6} - \frac{T_a \times f_{ao}'}{T_{ao} \times 10^6} \right) \tag{68}$$

is computed on the other half cycles. The frequency $f$ is the 1.0 MHz. clock frequency.

The AND gates 621 and 622 produce outputs on the counts of $$f_{ao} \times f_{ao}' \times 10^{-6} \tag{69}$$

and $$f_{go} \times f_{ao}' \times 10^{-6} \tag{70}$$

respectively.

One half cycle is about 1.0 second. The other is about ⅓ second.

What is claimed is:

1. A gravitometer comprising: a twin cell assembly having first and second chambers to house first and second fluids, respectively, of the same or different densities at substantially the same temperature and pressure; electromechanical feedback oscillator means including first and second vanes mounted in said first and second chambers, respectively, and means to oscillate both of said first and second vanes at the same or different first and second vibrational frequencies, respectively, said oscillator means having first and second output leads with first and second respective signals thereon of first and second respective frequencies directly proportional to said first and second vibrational frequencies, respectively, said first and second signals each having first annd second characteristic variables, said first and second variables of said first signal being the frequency $f_a$ thereof and the period $T_a$ thereof, respectively, said first and second variables of said second signal being the frequency $f_g$ thereof and the period $T_g$ thereof, respectively; and computer means connected from said oscillator means output leads having an output lead means for producing an output thereon directly proportional to the ratio of the density of said second fluid to that of said first fluid as a function of only the first variable of one signal and only the second variable of the other signal.

2. The invention as defined in claim 1, wherein said computer means produces an output directly proportional to G where $$G = K (T_g - T_{go})(f_a - f_{ao}')$$

where, $T_{go}$ is said second signal period when said second vane is in a vacuum, and $f_{ao}'$ is a constant.

3. The invention as defined in claim 2, wherein $$f_{ao}' \cong 2 f_c$$

where $f_c$ is the first signal frequency when said first vane vibrates in said first fluid at midrange density thereof.

4. The invention as defined in claim 3, wherein said midrange density is the density of air at about 760 mm. of mercury and about 20° C.

5. The invention as defined in claim 2, wherein $$f_{ao}' \cong \frac{f_c^2}{f_{ao}}$$

where, $f_{ao}$ is the first signal frequency when said first vane is in a vacuum, and $f_c$ is the first signal frequency when said first vane vibrates in said first fluid at a midrange density thereof.

6. The invention as defined in claim 5, wherein said midrange density is the density of air at about 760 mm. of mercury and about 20° C.

7. The invention as defined in claim 2, wherein said first and second signals include $f_a$ and $f_g$ pulses, respectively, said computer means including a clock having an output lead, said clock providing clock pulses at a constant pulse repetition frequency on said output lead thereof, first, second and third counters each having a counting input means connected from said clock output lead for simultaneously first admitting pulses on said oscillator means first output lead to said first counter counting input means while first admitting clock pulses to said second counter counting input means, means connected from said first counter for producing an $f_{ao}'$ output pulse at the first count of $f_{ao}'$, said second counter producing a first output pulse at a first constant predetermined number of said clock pulses, means for gating said $f_a$ pulses to the said third counter counting input means during a first interval of time between the occurence times of said $f_{ao}'$ output pulse and said second counter first output pulse, said first predetermined number being sufficiently large so as to cause said second counter first output pulse always to occur on or after said $f_{ao}'$ output pulse, cycle means connected from said second counter to cause said second counter first output pulse to reset both of said first and second counters, but not said third counter, the number of pulses counted by said third counter being stored therein, said cycle means causing said $f_g$ pulses to be admitted to said second counter counting input means on said reset thereof while admitting clock pulses to said first counter counting input means, means to produce a $T_{go}$ output pulse from said first counter upon the count $T_{go}$, said second counter producing a second output pulse after said $T_{go}$ pulse, a multiplier, means to gate said clock pulses to said multiplier during a second interval of time from said $T_{go}$ pulse to said second counter second output pulse, said multiplier being connected from said third counter to produce a number of output pulses responsive to said second interval clock pulses directly proportional to the product of the number thereof and said stored number, and adjustable calibration means connected from the output of said multiplier to multiply the number of output pulses exiting therefrom by a constant but adjustable factor, said computer means recycling said functions repeatedly, said second counter output pulse resetting all of said first, second and third counters to count again as aforesaid.

8. The invention as defined in claim 7, wherein utilization means are connected from the output of calibration means including an update counter to indicate the number of pulses in each group passed thereby.

9. The invention as defined in claim 8, wherein
$f_{ao}' \cong 2f_c$
where $f_c$ is the first signal frequency when said first vane vibrates in said first fluid at a midrange density thereof.

10. The invention as defined in claim 9, wherein said midrange density is the density of air at about 760 mm. of mercury and about 20° C.

11. The invention as defined in claim 8, wherein $$f_{ao}' \cong \frac{f_c^2}{f_{ao}}$$

where,
$f_{ao}$ is the first signal frequency when said first vane is in vacuum, and
$f_c$ is the first signal frequency when said first vane vibrates in said first fluid at a midrange density thereof.

12. The invention as defined in claim 11, wherein said midrange density is the density of air at about 760 mm. of mercury and about 20° C.

13. The invention as defined in claim 7, wherein
$f_{ao}' \cong 2f_c$
where $f_c$ is the first signal frequency when said first vane vibrates in said first fluid at a midrange density thereof.

14. The invention as defined in claim 13, wherein said midrange density is the density of air at about 760 mm. of mercury and about 20° C.

15. The invention as defined in claim 7, wherein $$f_{ao}' \cong \frac{f_c^2}{f_{ao}}$$

where,
$f_{ao}$ is the first signal frequency when said first vane is in a vacuum, and
$f_c$ is the first signal frequency when said first vane vibrates in said first fluid at a midrange density thereof.

16. The invention as defined in claim 15, wherein said midrange density is the density of air at about 760 mm. of mercury and about 20° C.

17. The invention as defined in claim 1, wherein said computer means produces an output directly proportional to G, where $$G = K \left( \frac{T_g}{T_{go}} - \frac{T_a}{T_{ao}} \right) f_a - f_{ao}' + B$$

where, $T_{go}$ is said second signal period when said second vane is in a vacuum,
$T_{ao}$ is said first signal period when said first vane is in a vacuum,
$f_{ao}'$ is a constant,
$K$ is a constant, and
$B$ is a constant.

18. The invention as defined in claim 17, wherein
$f_{ao}' \cong 2f_c$
where $f_c$ is the first signal frequency when said first vane vibrates in said first fluid at a midrange density thereof.

19. The invention as defined in claim 18, wherein said midrange density is the density of air at about 760 mm. of mercury and about 20° C.

20. The invention as defined in claim 17, wherein $$f_{ao}' \cong \frac{f_c^2}{f_{ao}}$$

where,
$f_{ao}$ is said first signal frequency when said first vane is in a vacuum, and
$f_c$ is the first signal frequency when said first vane vibrates in said first fluid at a midrange density thereof.

21. The invention as defined in claim 20, wherein said midrange density is the density of air at about 760 mm. of mercury and about 20° C.

22. A gravitometeer comprising: a twin cell assembly having first and second chambers to house first and second fluids, respectively, of the same or different densities at substantially the same temperature and pressure; electromechanical feedback oscillator means including first and second vanes mounted in said first and second chambers, respectively, and means to oscillate both of said first and second vanes at the same or different first and second vibrational frequencies, respectively, said oscillator means having first and second output leads with first and second respective signals thereon of first and second respective frequencies directly proportional to said first and second vibrational frequencies, respectively, said first and second signals each having first and second characteristic variables, said first and second variables of said first signal being the frequency $f_a$ thereof and the period $T_a$ thereof, respectively, said first and second variables of said second signal being the frequency $f_g$ thereof and the period $T_g$ thereof, respectively; and computer means connected from said oscillator means output leads having an output lead means for producing an output signal thereon directly proportional to the ratio of the density of said second fluid to that of said first fluid as a function of only the second variable of one signal and at least one variable of the other signal.

23. The invention as defined in claim 22, wherein said computer means produces an output directly proportional to the product
$(T_g - T_{go})(T_{ao}' - T_a)$
where,
$T_{go}$ is the second signal period when said second vane is in a vacuum, and
$T_{ao}'$ is a constant.

24. The invention as defined in claim 23, wherein
$T_{ao}' \cong 2T_c - T_{ao}$
where, $T_c$ is the first signal period when said first vane is in said first fluid in air at a standard midrange density thereof, and $T_{ao}$ is the first signal period when said first vane is in a vacuum.

25. The invention as defined in claim 22, wherein said computer means produces an output directly proportional to G, where $$G = [K]\left[\frac{T_g}{T_{go}} - \frac{T_a}{T_{ao}}\right] + B$$

where,

K is a constant,

B is a constant, $T_{ao}$ is the frequency of said first signal when said first vane is in a vacuum, and $T_{go}$ is the period of said second signal when said second vane is in a vacuum.

26. A gravitometer comprising: a twin cell assembly having first and second chambers to house first and second fluids, respectively, of the same or different densities at substantially the same temperature and pressure; electromechanical feedback oscillator means including first and second vanes mounted in said first and second chambers, respectively, and driver means to oscillate both of said first and second vanes at the same or different first and second vibrational frequencies, respectively, said oscillator means having first and second output leads with first and second respective signals thereon of first and second respective frequencies directly proportional to said first and second vibrational frequencies, respectively, said first and second signals each having first and second characteristic variables, said first and second variables of said first signal being the frequency $f_a$ and the period $T_a$ thereof, respectively, said first and second variables of said second signal being the frequency $f_g$ thereof and the period $T_g$ thereof, respectively; and computer means connected from said oscillator means output leads having an output lead means for producing an output thereon directly proportional to the ratio of the density of said second fluid to that of said first fluid as a function of at least one of said first signal variables and at least one of said second signal variables, said oscillator means including first and second sensors having first and second output leads, respectively, to produce electrical output signals of first and second frequencies, respectively, thereon equal to the said first and second vibrational frequencies, respectively, first and second phase lock loops having first and second input leads connected from the respective first and second output leads of said sensors, said first and second phase lock loops having first and second respective output leads, said driver means being connected from said first and second phase lock loops to vibrate both of said vanes at the same or different vibrational frequencies.

27. The invention as defined in claim 26, wherein said oscillator means first and second output leads are connected from said first and second phase lock loops, respectively, to said computer means, said first phase lock loop producing a signal on said oscillator means first output lead of a frequency directly proportional to, but larger than, said first vibrational frequency, said second phase lock loop producing a signal on said oscillator means second output lead of a frequency directly proportional to, but larger than, said first vibrational frequency.

28. The invention as defined in claim 27, wherein said first phase lock loop includes a first phase detector, a first low pass filter, a first voltage controlled oscillator (VCO) and a first frequency divider connected in succession in that order from said first sensor, said first frequency divider having an output lead connected to an input lead of said first phase detector, said driver means being connected from said first frequency divider output lead, said first frequency divider having an input lead connected from an output lead of said first VCO, said oscillator means first output being connected from said first VCO output lead.

29. The invention as defined in claim 28, wherein said second phase lock loop includes a second phase detector, a second low pass filter, a second voltage controlled oscillator and a second frequency divider connected in succession in that order from said second sensor, said second frequency divider having an output lead connected to an input lead of said second phase detector, said driver means being connected from said second frequency divider output lead, said second frequency divider having an input lead connected from an output lead of said second VCO, said oscillator means second output lead being connected from said second VCO output lead.

30. A gravitometer comprising: a supporting body; first and second ferromagnetic members mounted on said body in a position to vibrate; a ferromagnetic driver including a coil, said electromagnetic driver being fixed relative to said body in a position to establish a magnetic field to attract both of said ferromagnetic members when said coil is energized; first and second devices mounted on said body to produce first and second AC electrical output signals, respectively, of first and second frequencies, respectively, of first and second frequencies of vibration of said first and second members, respectively; a coil input junction, said coil being connected from said coil input junction; and driver means connected from both of said devices to said coil input junction for impressing an AC voltage on said coil input junction to establish an AC component of current through said coil, said driver means including a source connected to said coil input junction to supply thereto a DC component of current in addition to the said AC component of current, said AC component of current modulating the intensity of said magnetic field in a manner to cause both of said ferromagnetic members to vibrate, said source causing said first and second devices to produce first and second output signals of frequencies equal to said vibrational frequencies of said first and second members, respectively, said ferromagnetic driver including said coil, said magnetic field, said ferromagnetic members, said devices, and said driver means forming a closed loop electromechanical oscillator, said driver means including an amplifier having a gain adequate to sustain vibration of both of said members continuously; and temperature sensitive means to vary said DC component of current in a direction such that the product $(T_g - T_{go})(f_a - f_{ao})$ varies less with temperature than when said DC component of current is constant, $T_g$ being the period of vibration of said first member, $T_{go}$ being the vacuum period of said first member, $f_a$ being the vibrational frequency of said second member, and $f_{ao}$ is a constant.

31. The invention as defined in claim 30, wherein said source is adapted to supply said coil with current in a manner such that the magnitude of said DC component of current exceeds the peak value of said AC component of current.

32. The invention as defined in claim 31, wherein said driver means includes zero apparatus to adjust the magnitude of said DC component of current.

33. The invention as defined in claim 32, wherein said driver means includes span apparatus to adjust the rate of change of said DC component of current with respect to temperature.

34. The invention as defined in claim 31, wherein said driver means includes span apparatus to adjust the rate of change of said DC component of current with respect to temperature.

* * * * *